US009988329B1

(12) United States Patent
Janka et al.

(10) Patent No.: US 9,988,329 B1
(45) Date of Patent: Jun. 5, 2018

(54) TRANSFER-HYDROGENATION PROCESS

(71) Applicant: Eastman Chemical Company, Kingsport, TN (US)

(72) Inventors: Mesfin Ejerssa Janka, Kingsport, TN (US); Robert Thomas Hembre, Johnson City, TN (US); Scott Donald Barnicki, Kingsport, TN (US); Robert Scott Huss, Kingsport, TN (US); Xiaopeng Shan, Plano, TX (US); Stephanie Rollins Testerman, Kingsport, TN (US); Timothy Alan Upshaw, Kingsport, TN (US); Dewey Wayne Fuller, Jr., Bristol, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days. days.

(21) Appl. No.: 15/427,691

(22) Filed: Feb. 8, 2017

(51) Int. Cl.
| | |
|---|---|
| *C07C 29/14* | (2006.01) |
| *C07C 29/50* | (2006.01) |
| *C07C 45/62* | (2006.01) |
| *C07C 51/00* | (2006.01) |
| *C07C 29/80* | (2006.01) |
| *C07C 45/82* | (2006.01) |
| *C07C 51/44* | (2006.01) |
| *B01J 23/755* | (2006.01) |
| *B01J 23/883* | (2006.01) |
| *B01J 23/887* | (2006.01) |

(52) U.S. Cl.
CPC ............. *C07C 29/14* (2013.01); *B01J 23/755* (2013.01); *B01J 23/883* (2013.01); *B01J 23/8878* (2013.01); *C07C 29/80* (2013.01); *C07C 45/62* (2013.01); *C07C 45/82* (2013.01); *C07C 51/00* (2013.01); *C07C 51/44* (2013.01)

(58) Field of Classification Search
CPC ......... C07C 29/14; C07C 29/80; C07C 45/62; C07C 45/82
See application file for complete search history.

(56) References Cited

U.S. PATENT DOCUMENTS

| | | | |
|---|---|---|---|
| 2,060,267 A | 11/1936 | Toussaint | |
| 4,701,562 A * | 10/1987 | Olson | .................. C07C 45/002 568/390 |
| 6,008,416 A | 12/1999 | Lawson et al. | |
| 6,518,462 B2 | 2/2003 | Saayman et al. | |

OTHER PUBLICATIONS

Sharma, M.M. et al.; "Industrial Applications of Reactive Distillation"; Reactive Distillation; Wiley-VCH; 2002; pp. 3-29.
Harmsen; "Reactive distillation: The front-runner of industrial process intensification a full review of commercial applications, research, scale-up, design and operation"; Chemical Engineering and Processing; 46; 2007; pp. 774-780.
Lutze, Philip et al.; "Heterogeneous Catalytic Distillation—A Patent Review"; Recent Patents on Chemical Engineering; 2010; 3; pp. 208-229.
O'Keefe, W.K. et al.; "Experimental Studies on the Syntheses of Mesityl Oxide and Methyl Isobutyl Ketone via Catalytic Distillation"; Ind. Eng. Chem. Res.; 2007; 46; pp. 716-725.
Gliński, Marek et al.; "Reactivity of Alcohols in Chemoselective Transfer Hydrogenation of Acrolein over Magnesium Oxide as the Catalyst"; Catal. Lett.; 2011; 141; pp. 293-299.
Darwish, Muftah et al.; "Asymmetric catalysis using iron complexes—'Ruthenium Lite'?"; Catalysis Science & Technology; 2012; 2; pp. 243-255.
Saidi, Ourida et al.; "Iridium-Catalyzed Hydrogen Transfer Reactions"; Top Organomet Chem.; 2011; 34; pp. 77-106.
Samec, Joseph S.M. et al.; "Mechanistic aspects of transition metal-catalyzed hydrogen transfer reactions"; Chemical Society Reviews; 2006; 35; pp. 237-248.
Shi, Ruijuan et al.; "A highly efficient Cu/La2O3 catalyst for transfer dehydrogenation of primary aliphatic alcohols"; Green Chemistry; 2010; 12; pp. 108-113.

* cited by examiner

*Primary Examiner* — Sikarl A Witherspoon
(74) *Attorney, Agent, or Firm* — Matthew W. Smith

(57) ABSTRACT

A transfer-hydrogenation process for preparing a carbonyl compound and an alcohol compound comprises the steps of (a) contacting a first carbonyl compound with a first alcohol compound in the presence of a transfer-hydrogenation catalyst in a first reaction zone at conditions effective to form a second carbonyl compound from the first alcohol compound and a second alcohol compound from the first carbonyl compound, and (b) removing the second carbonyl compound from the first reaction zone during step (a). The first carbonyl compound is a saturated aldehyde or ketone, or an α,β-unsaturated aldehyde or ketone. The first alcohol compound is a primary or secondary alcohol. The second alcohol compound is α,β-saturated. The transfer-hydrogenation catalyst includes a Group 8 to 11 metal. This process is useful for preparing and higher value alcohols, such as butanol or 2-ethylhexanol, from the corresponding carbonyl compounds by engaging lower alcohol ($C_2$-$C_4$) feedstocks instead of hydrogen ($H_2$).

23 Claims, 1 Drawing Sheet

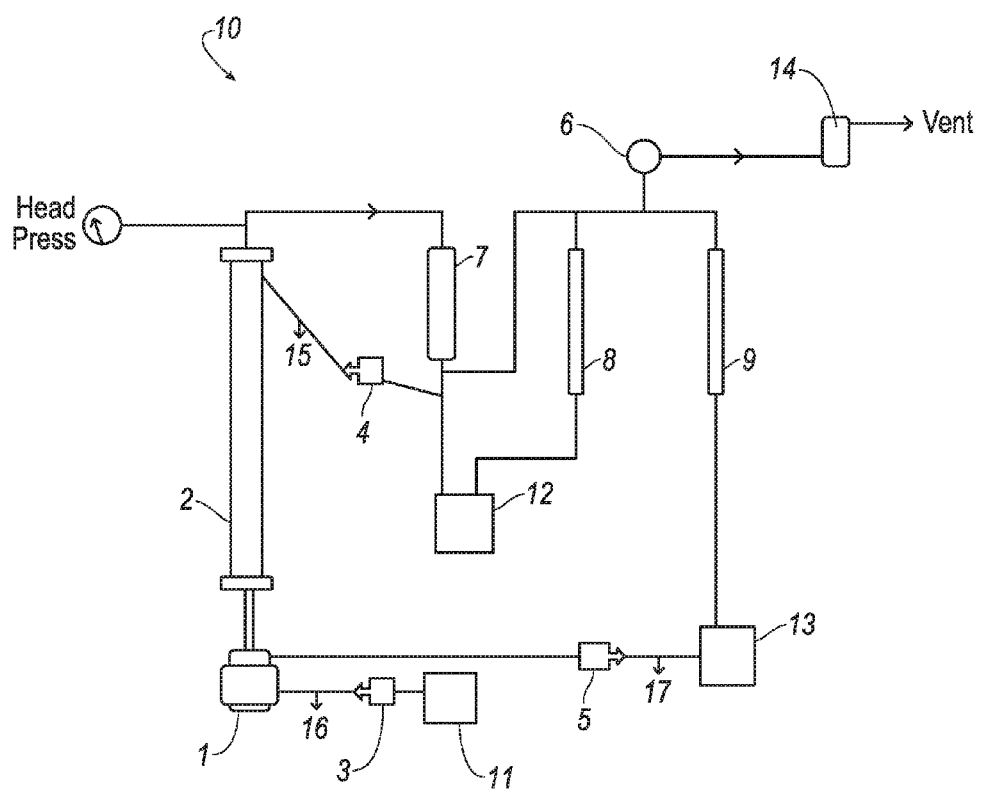

TRANSFER-HYDROGENATION PROCESS

FIELD OF THE INVENTION

The invention generally relates to the field of transfer-hydrogenation and, more particularly, to the field of catalytic hydrogen transfer from alcohol compounds to carbonyl compounds.

BACKGROUND OF THE INVENTION

In a "transfer-hydrogenation," a "hydrogen donor" provides a H2-equivalent that is transferred to a recipient. This reaction is illustrated below for the transfer of hydrogen from an alcohol to an aldehyde or ketone.

$$\underset{H_2\text{-acceptor}}{\overset{O}{\underset{R_1}{\|}}\!\!\!\!\!\underset{R_2}{C}} + \underset{H_2\text{-donor}}{R_3-\underset{H}{\overset{OH}{\underset{|}{C}}}-R_4} \xrightarrow{\text{transfer-hydrogenation catalyst}}$$

$$\underset{\text{reduced product}}{R_1-\underset{H}{\overset{OH}{\underset{|}{C}}}-R_2} + \underset{\text{oxidized donor}}{\overset{O}{\underset{R_3}{\|}}\!\!\!\!\!\underset{R_4}{C}}$$

Because the reactants and the products are both a mixture of alcohols and carbonyls, the reaction equilibrium may be modest and can limit the conversion. It has been common in the art of transfer-hydrogenation to employ a large excess of the donor alcohol to favor higher conversion of the acceptor to the saturated alcohol product. The excess alcohol, however, leads to added expense, which is required to separate, recover, and recycle the donor alcohol.

Thus, there is a need for a more economical and efficient transfer-hydrogenation process, particularly one that does not require a large excess of the donor alcohol.

The present invention addresses this need as well as others, which will become apparent from the following description and the appended claims.

SUMMARY OF THE INVENTION

The invention is as set forth in the appended claims.

Briefly, the invention provides a process for preparing a carbonyl compound and an alcohol compound. The process comprises the steps of:

(a) contacting a first carbonyl compound with a first alcohol compound in the presence of a transfer-hydrogenation catalyst in a first reaction zone at conditions effective to form a second carbonyl compound from the first alcohol compound and a second alcohol compound from the first carbonyl compound; and (b) removing the second carbonyl compound from the first reaction zone during step (a), wherein the first carbonyl compound is a saturated aldehyde or ketone, or an α,β-unsaturated aldehyde or ketone, wherein the first alcohol compound is a primary or secondary alcohol, wherein the second alcohol compound is α,β-saturated, and wherein the transfer-hydrogenation catalyst comprises a Group 8 to 11 metal.

In one embodiment, the process further comprises the steps of:

(c) condensing the second carbonyl compound in an aldol condensation reaction to produce the first carbonyl compound; and (d) passing the first carbonyl compound from the aldol condensation reaction to step (a).

In another embodiment, the process further comprises the steps of:

(e) contacting a third carbonyl compound with the second alcohol compound in the presence of a second transfer-hydrogenation catalyst in a second reaction zone at conditions effective to form a fourth carbonyl compound from the second alcohol compound and a third alcohol compound from the third carbonyl compound;

(f) removing the fourth carbonyl compound from the second reaction zone during step (e), (g) condensing the fourth carbonyl compound in an aldol condensation reaction to produce the third carbonyl compound; and (h) passing the third carbonyl compound from the aldol condensation reaction to step (e).

The process according to the invention may be advantageously carried out in one or more reactive distillation columns.

BRIEF DESCRIPTION OF THE DRAWING

FIG. 1 shows a continuous reactive distillation unit (10) used in the working examples.

DETAILED DESCRIPTION OF THE INVENTION

As noted above, a barrier to effectively using transfer-hydrogenation in making higher molecular weight and higher value alcohols is the near neutral and sometimes unfavorable, alcohol-to-carbonyl transfer-hydrogenation reaction equilibrium. This problem has been addressed most often by using a large excess of alcohol to drive the equilibrium. Using excess alcohol, however, can add cost and complication to the process, since the unreacted alcohol has to be separated, recovered, and recycled.

It has been surprisingly discovered, however, that continuously removing the low-boiling, carbonyl product as it is formed during the transfer-hydrogenation reaction can both drive the equilibrium and provide easy separation/purification of the desired products.

Therefore, according to the invention, the transfer-hydrogenation process is advantageously carried out in an apparatus that is configured to distill the low-boiling product and separate it from the reaction mixture coincident with the progress of the transfer-hydrogenation reaction.

Such an apparatus can be as simple as a stirred reactor fitted with a fractionation column for removing the low-boiling carbonyl product. The reaction vessel can also contain multiple ports for reactant introduction and product removal.

In one embodiment, the reactor is fitted with a fractionation column and access ports for charging the reactants and the transfer-hydrogenation catalyst.

Another apparatus suitable for use in the present invention includes a reactive distillation column. Reactive distillation is a powerful technique for process intensification. It has been applied to a wide range of chemical reactions including esterification, amidation, etherification, isomerization, alkylation, nitration, aldol condensation, acetalization, olefin metathesis, and hydrogenation providing continuous process technology in which chemical reaction steps are integrated with product separation in a single unit operation. These and other applications have been reviewed by Sharma and Mahajani (*Reactive Distillation*, Wiley VCH, pp. 3-29 (2002)) and Harmsen (*Chem. Eng. Proc.* 46, 774-80 (2007)). When a heterogeneous catalyst is used and serves both as a catalyst for the reaction and a packing material for the distillation, the process is often referred to as a "catalytic distillation" (Lutze et al., *Rec. Pat. Chem. Eng.*, 3, 208-29 (2010)).

As applied to transfer-hydrogenation, it has been surprisingly found that "reactive distillation" or "catalytic distillation" can overcome the thermodynamic limits of transfer-hydrogenation and can allow highly efficient reduction of α,β-unsaturated aldehydes and ketones. In reactive- or catalytic-distillation, a chemical reaction is carried out coincident with a distillation process. As the alcohol and carbonyl products are distilled away from the reactants and intermediates under reaction conditions in the presence of a catalyst that catalyzes the equilibrium, the conversion can be driven by this selective removal of products.

Thus, in one aspect, the invention provides a process for preparing a carbonyl compound and an alcohol compound. The process comprises the steps of:

(a) contacting a first carbonyl compound with a first alcohol compound in the presence of a transfer-hydrogenation catalyst in a first reaction zone at conditions effective to form a second carbonyl compound from the first alcohol compound and a second alcohol compound from the first carbonyl compound; and (b) removing the second carbonyl compound from the first reaction zone during step (a), i.e., during the transfer-hydrogenation reaction.

The first carbonyl compound can be a saturated aldehyde or ketone, or an α,β-unsaturated aldehyde or ketone. In one embodiment, the first carbonyl compound comprises a saturated aldehyde or an α,β-unsaturated aldehyde. In another embodiment, the first carbonyl compound comprises a saturated ketone or an α,β-unsaturated ketone.

In one embodiment, the first carbonyl compound is represented by the formula (I):

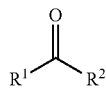

(I)

wherein $R^1$ is hydrogen, an alkyl group having 1-16 carbon atoms, or an aryl group having 6-20 carbon atoms; and $R^2$ is an alkyl group having 1-16 carbon atoms, an aryl group having 6-20 carbon atoms, or an α,β-alkenyl group having 2-16 carbon atoms.

The alkyl groups represented by $R^1$ and $R^2$ may independently be branched or unbranched. The aryl groups represented by $R^1$ and $R^2$ may independently be substituted or unsubstituted. Examples of substituents on the aryl groups include alkyl groups (examples of the alkyl groups include ethyl, butyl, pentyl, hexyl, 2-ethylhexyl, octyl, decyl, dodecyl, octadecyl and various isomers thereof), alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like.

The α,β-alkenyl group represented by $R^2$ may be branched or unbranched.

Examples of carbonyl compounds having the formula (I) include crotonaldehyde, mesityl oxide, butylidene acetone, isobutylidene acetone, 2,6-dimethylhepta-2,5-dien-4-one, 2-methyl-2-pentenal, 2-ethyl-2-hexenal, 2-propyl-2-heptenal, and 2,4-dimethyl-2-heptenal. Additional examples of carbonyl compounds having the formula (I) include methyl propyl ketone, methyl isopropyl ketone, methyl isobutyl ketone, methyl amyl ketone, diisobutyl ketone, diamyl ketone, diisoamyl ketone, 3-methylcyclohexanone, 3,5-dimethylcyclohexanone, 3-methyl-3-propylcyclohexanone, 3-methyl-3-isopropylcyclohexanone, 3,5,5-trimethylcyclohexanone, 4,6-dimethyl-2-heptanone, 4-methyl-2-nonanone, 2-methyl-4-nonanone, 4-heptanone, 4-methyl-2-heptanone, and 2-methyl-4-heptanone.

In one particular embodiment, the first carbonyl compound is crotonaldehyde or 2-ethyl-2-hexenal.

The first alcohol compound is desirably a primary or secondary alcohol. Preferably, the alcohol is derived from a renewable resource.

In one embodiment, the first alcohol compound is an iso-alcohol.

The first alcohol compound may have the formula (II):

(II)

wherein $R^3$ is hydrogen, an alkyl group having 1-16 carbon atoms, or an aryl group having 6-20 carbon atoms; and $R^4$ is an alkyl group having 1-16 carbon atoms or an aryl group having 6-20 carbon atoms.

The alkyl groups represented by $R^3$ and $R^4$ may independently be branched or unbranched. The aryl groups represented by $R^3$ and $R^4$ may independently be substituted or unsubstituted. Examples of substituents on the aryl groups include alkyl groups (examples of the alkyl groups include ethyl, butyl, pentyl, hexyl, 2-ethylhexyl, octyl, decyl, dodecyl, octadecyl and various isomers thereof), alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like.

Examples of alcohol compounds having the formula (II) include ethanol, n-propanol, iso-propanol, n-butanol, iso-butanol, n-pentanol, iso-pentanol, n-hexanol, and 2-ethylhexanol.

In one embodiment, the first alcohol compound has 2 to 8 carbon atoms.

In another embodiment, the first alcohol compound has 2 to 4 carbon atoms, such as ethanol, n-propanol, iso-propanol, n-butanol, and iso-butanol.

In yet another embodiment, the first carbonyl compound is crotonaldehyde or 2-ethyl-2-hexenal, and the first alcohol compound is ethanol, n-butanol, or iso-butanol.

In yet another embodiment, the first carbonyl compound is 2-ethyl-2-hexenal, and the first alcohol compound is iso-butanol.

In yet another embodiment, the first carbonyl compound is methyl propyl ketone, methyl isopropyl ketone, methyl isobutyl ketone (MIBK), methyl amyl ketone (MAK), diisobutyl ketone (DIBK), diamyl ketone, diisoamyl ketone, 3-methylcyclohexanone, 3,5-dimethylcyclohexanone, 3-methyl-3-propylcyclohexanone, 3-methyl-3-isopropylcyclohexanone, 3,5,5-trimethylcyclohexanone, 4,6-dimethyl-2-heptanone, 4-methyl-2-nonanone, 2-methyl-4-nonanone, 4-heptanone, 4-methyl-2-heptanone, or 2-methyl-4-heptanone; and the first alcohol compound is isopropanol. In this embodiment, the transfer-hydrogenation reaction would produce an alcohol compound corresponding to the ketone reactant (e.g., methyl isobutyl carbinol from MIBK, diisobutyl carbinol from DIBK, or methyl amyl carbinol from MAK), and the isopropanol would convert to acetone.

The second alcohol compound, which is derived from the first carbonyl compound, is α,β-saturated.

The second alcohol compound may have the formula (III):

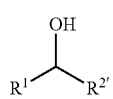

wherein $R^1$ is as defined above in connection with the formula (I); and $R^{2'}$ is an alkyl group having 1-16 carbon atoms or an aryl group having 6-20 carbon atoms.

The alkyl groups represented by $R^{2'}$ may be branched or unbranched. The aryl groups represented by $R^{2'}$ may be substituted or unsubstituted. Examples of substituents on the aryl groups include alkyl groups (examples of the alkyl groups include ethyl, butyl, pentyl, hexyl, 2-ethylhexyl, octyl, decyl, dodecyl, octadecyl and various isomers thereof), alkoxy, cycloalkoxy, formyl, alkanoyl, cycloalkyl, aryl, aryloxy, aroyl, carboxyl, carboxylate salts, alkoxycarbonyl, alkanoyloxy, cyano, sulfonic acid, sulfonate salts, and the like.

In one embodiment, the second alcohol compound is saturated.

In another embodiment, the second alcohol compound is n-butanol or 2-ethylhexanol.

The second carbonyl compound, which is derived from the first alcohol compound, is an aldehyde or a ketone. It may have the formula (IV):

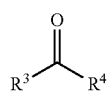

wherein $R^3$ and $R^4$ are as defined above in connection with the formula (II).

In one embodiment, the second carbonyl compound is acetaldehyde or n-butyraldehyde.

In another embodiment, the second carbonyl compound has the lowest boiling point and the second alcohol compound has the highest boiling point among all reactants, products, and by-products in the first reaction zone.

In yet another embodiment, the first alcohol compound is an iso-alcohol and the second carbonyl compound is an aldehyde or a ketone.

The process according to the invention does not require a large excess of alcohol to drive the equilibrium. Generally, a feed mixture containing an alcohol-to-carbonyl molar ratio of 10:1 to 0.5:1 may be used. Exemplary alcohol-to-carbonyl molar ratios in the feed mixture include 9:1, 8:1, 7:1, 6:1, 5:1, 4:1, 3:1, 2:1, 1:1, 0.9:1, 0.8:1, 0.7:1, and 0.6:1.

Typical transfer-hydrogenation conditions include atmospheric pressure and elevated temperature. The temperature for reaction is typically set based on the lowest boiling point of the reactants, which can be either the feed alcohol or the feed carbonyl compound. Generally, the temperature for reaction can range, for example, from 50 to 250° C., or from 100 to 200° C.

The transfer-hydrogenation catalyst comprises a Group 8 to 11 metal as the primary catalytic component. In one embodiment, the transfer-hydrogen catalyst comprises cobalt, nickel, copper, palladium, platinum, ruthenium, iridium, or combinations thereof.

The transfer-hydrogenation catalyst may be a homogeneous catalyst or a heterogeneous catalyst.

The transfer-hydrogenation catalyst may further include a Group 6 metal (such as chromium or molybdenum) as a promoter.

In one embodiment, the transfer-hydrogenation catalyst includes a Sponge Metal™ catalyst, available from Johnson Matthey. Such catalysts are believed to be prepared from alloys of transition metals and aluminum. The aluminum is leached from the alloy structure, leaving behind an active metal surface covered or saturated with adsorbed hydrogen. The activated catalysts are stored under water to protect them from oxidation. The Sponge Metal™ catalysts are in a fully active form when shipped.

The particle size of the heterogeneous catalyst useful in the invention is not particularly limiting. Typically, the heterogeneous catalyst may have a median particle size ranging from 10 to 200 μm.

In general, the rate of reaction increases with increasing catalyst concentration. Because heterogeneous catalysts are easily separated from the reaction mixture, they can be used at higher levels to achieve shorter reaction times and lower temperatures. Although the catalyst may be present in amounts as low as to provide a minimum of 0.001 mole of metal(s) loading per mole of substrate, greater proportions of catalyst, approaching or exceeding one mole of metal(s) loading per mole of reactant, can be used to achieve higher reaction rates. In one embodiment of the process of the invention, for example, the process can be operated as a continuous process in which the maximum allowable catalyst concentration is limited only by the weight of catalyst which may be packed into the volume of the transfer-hydrogenation reaction zone while preserving effective contact of reactants and practical flow rates.

Examples of homogeneous transfer-hydrogenation catalysts may be found in reviews by Martin Wills (*Catal. Sci. & Tech.*, 2, 243 (2012)), Jon Williams (*Top. Organomet. Chem.*, 34, 77 (2011)), and Jan Bäckvall (*Chem. Soc. Rev.*, 35, 237 (2006)), for instance. Specific examples of homogeneous catalysts include $H_2Ru(PPh_3)_4$, $Ru_3(CO)_{12}$, $(Ph_4C_4CO)Ru(CO)_3$, $[(4-ClC_6H_4)_4C_4CO]Ru(CO)_3$, $[2,5-(C_6H_4)_2-3,4-(4-MeOC_6H_4)_2C_4CO]Ru(CO)_3$, $[2,5-(C_6H_4)_2-3,4-(4-FC_6H_4)_2C_4CO]Ru(CO)_3$, $(Ph_4C_4CO)_2H(\mu-H)(CO)_4Ru_2$, $[(4-ClC_6H_4)_4C_4CO]_2H(\mu-H)(CO)_4Ru_2$, $[2,5-(C_6H_4)_2-3,4-(4-MeOC_6H_4)_2C_4CO]_2H(\mu-H)(CO)_4Ru_2$, and $[2,5-(C_6H_4)_2-3,4-(4-FC_6H_4)_2C_4CO]_2H(\mu-H)(CO)_4Ru_2$.

The transfer-hydrogenation process may be practiced in a batch or continuous mode.

As noted, the process according to the invention is advantageously carried out in a reactor equipped with a fractionation column or in a reactive distillation column. Either type of column can have, for example, from 2 to 50 theoretical stages, 5 to 40 theoretical stages, 10 to 30 theoretical stages, or 10 to 20 theoretical stages.

In the case of a reactive distillation column, the reactants are preferably introduced into the column at one or more of the intermediate stages. For example, in one embodiment, a reactive distillation column having 15 theoretical stages is employed. In which case, the first carbonyl compound and the first alcohol compound may be introduced into the column at one or more theoretical stages 7 through 12, counting from top to bottom.

In another reactive distillation embodiment, the second carbonyl compound is withdrawn from the column in an overhead stream and the second alcohol compound is withdrawn from the column in a bottoms stream.

Carrying out transfer-hydrogenation in a reactive distillation column or in a reactor plus fractionation column offers a number of advantages. For example, it allows "hydrogenation" to be accomplished without using hydrogen gas or elevated pressures. During the reaction, removing a low-boiling oxidized product of hydrogen donation (i.e., the second carbonyl compound) allows the hydrogenation equilibrium to be driven towards high conversion without needing a large excess of the reducing agent (i.e., the first alcohol compound) or high pressure, as in the use of hydrogen gas. In addition, a facility employing a distillation or fractionation column can offer an improvement in safety by avoiding the transfer and storage of hydrogen gas. Moreover, the by-products of the hydrogenation are valuable carbonyls which, when derived from renewable feedstocks, are bio-carbonyl resources capable of conversion to many valuable bio-derivatives.

The process according to one or more embodiments of the invention is capable producing the second alcohol compound at a selectivity (on a molar basis) of at least 50%, at least 60%, at least 70%, at least 80%, at least 90%, at least 95%, or at least 97%.

The process according to one or more embodiments of the invention is capable producing the second alcohol compound at a yield (on a molar basis) of at least 50%, at least 60%, at least 70%, at least 80%, at least 90%, at least 95%, or at least 97%.

The process according to one or more embodiments of the invention is capable producing more saturated alcohol than unsaturated alcohol. For example, the process according to one or more embodiments of the invention can produce at least 2 times, at least 3 times, at least 4 times, at least 5 times, or at least 10 times more saturated alcohol than unsaturated alcohol.

The process according to one or more embodiments of the invention can provide a selectivity (on a molar basis) to an allyl alcohol as a by-product of less than 10%, less than 5%, or less than 2%.

One hydrogen acceptor of specific interest is crotonaldehyde (see Eq. 1 below).

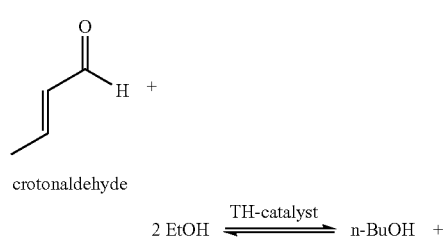

crotonaldehyde

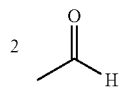

As shown in Equation 1, the transfer-hydrogenation of crotonaldehyde with ethanol produces n-butanol (n-BuOH) and acetaldehyde. In a separate step, the acetaldehyde can be condensed to produce additional crotonaldehyde, which can be recycled. Thus, in a second aspect, the invention includes a two-step process for making a higher alcohol using a lower alcohol. Step one involves transfer-hydrogenating crotonaldehyde with ethanol, and step two involves aldol condensing acetaldehyde to produce additional crotonaldehyde. Because the product of the aldol condensation (crotonaldehyde) is a feed for the transfer-hydrogenation, and because the volatile product of the transfer-hydrogenation (acetaldehyde) is the feed for the aldol condensation, the two-step process defines a cycle in which ethanol can be used to make butanol.

Another hydrogen acceptor of specific interest is 2-ethyl-2-hexenal (2EHenal, see Eq. 2 below).

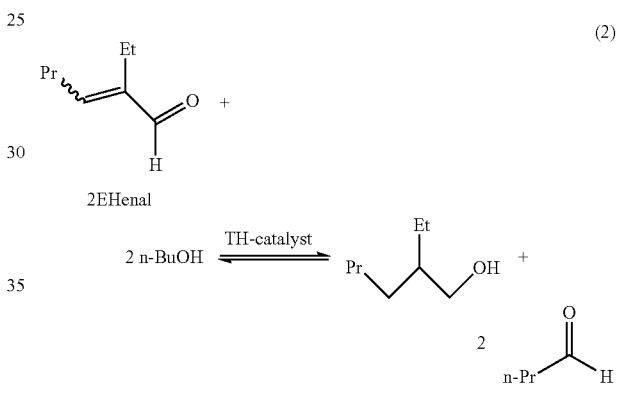

As seen in Equation 2, when n-BuOH is the hydrogen donor for the reduction of 2EHenal, the oxidized product is n-butyraldehyde and the fully reduced product is 2-ethylhexanol (2EH). In the same way as described above with crotonaldehyde, when n-butyraldehyde (the most volatile component of Eq. 2) is subjected to an aldol condensation in a separate step, it produces additional 2EHenal, which can be used as a feed for the transfer hydrogenation described by Equation 2. Thus, Equation 2 defines an analogous cyclic, two-step process in which n-BuOH can be used to form 2EH.

Thus, in one embodiment, in addition to steps (a)-(b) above, the process according to the invention may further comprise the steps of:

(c) condensing the second carbonyl compound in an aldol condensation reaction to produce the first carbonyl compound; and (d) passing the first carbonyl compound from the aldol condensation reaction to step (a).

In the case of Equation 1, the first carbonyl compound is crotonaldehyde, the first alcohol compound is ethanol, the second alcohol compound is n-butanol, and the second carbonyl compound is acetaldehyde.

In the case of Equation 2, the first carbonyl compound is 2-ethyl-2-hexenal, the first alcohol compound is n-butanol, the second alcohol compound is 2-ethylhexanol, and the second carbonyl compound is n-butyraldehyde.

During the condensing step (c), water may be removed from the reaction mixture. Additionally, or alternatively, water can be separated from the first carbonyl compound before the first carbonyl compound is recycled to step (a).

Water may be removed from the reaction mixture during the condensing step (c) by using a reactor equipped with fractionation column or a reactive distillation column. Any residual water can be separated from the first carbonyl compound before the first carbonyl compound is recycled to step (a) by using conventional separation/purification techniques, such as decantation or distillation.

The aldol reaction can be carried out in presence of a catalyst at a temperature ranging from room temperature to 200° C. and a pressure ranging from atmospheric pressure to 1000 psig (6.9 MPa). Any catalyst known in the art to catalyze the aldol reaction can be utilized to catalyze the reaction.

In addition to water removal, the crude aldol product can be further purified by distillation, extraction, decantation, or any other purification techniques known in the art before recycling to step (a).

Because the fully reduced product of Equation 1 (n-butanol) is the hydrogen donor in Equation 2, the invention further includes a four-step ethanol-to-2EH process, which results from the combination of the two two-step processes described above. This four-step process has particular value due to the abundant availability of ethanol as an article of commerce and the high demand for 2EH as a component of plasticizers.

In particular, the ability to produce n-butanol from ethanol in high yield (albeit indirectly) is desirable as the first step of a four-step process to produce 2EH from ethanol (indirectly). Ethanol can be used to transfer-hydrogenate crotonaldehyde to n-butanol. Then, the resulting acetaldehyde can be subjected to aldol condensation to produce crotonaldehyde as a feed for the first step. In the third step, n-butanol can be used to transfer-hydrogenate 2EHenal to 2EH, and the resulting butyraldehyde can be subjected to aldol condensation to produce 2EHenal as a feed for the third step. Depending on the supply and demand for bio-ethanol in the future and the resulting cost of ethanol, this four-step process is a very attractive approach to making 2EH.

Thus, in one embodiment, in addition to steps (a)-(d) above, the process according to the invention may further comprise the steps of:

(e) contacting a third carbonyl compound with the second alcohol compound in the presence of a second transfer-hydrogenation catalyst in a second reaction zone at conditions effective to form a fourth carbonyl compound from the second alcohol compound and a third alcohol compound from the third carbonyl compound;

(f) removing the fourth carbonyl compound from the second reaction zone during step (e), (g) condensing the fourth carbonyl compound in an aldol condensation reaction to produce the third carbonyl compound; and (h) passing the third carbonyl compound from the aldol condensation reaction to step (e).

In one particular embodiment of the process containing steps (a)-(h), the first carbonyl compound can be crotonaldehyde, the first alcohol compound can be ethanol, the second alcohol compound can be n-butanol, the second carbonyl compound can be acetaldehyde, the third carbonyl compound can be 2-ethyl-2-hexenal, the third alcohol compound can be 2-ethylhexanol, and the fourth carbonyl compound can be n-butyraldehyde.

The second transfer-hydrogenation catalyst can be the same as or different from the first transfer-hydrogenation catalyst. Generally, it may comprise a Group 8 to 11 metal, such as cobalt, nickel, copper, palladium, platinum, ruthenium, iridium, or combinations thereof.

Like the first transfer-hydrogenation catalyst, the second transfer-hydrogenation catalyst may be homogeneous or heterogeneous.

The second transfer-hydrogenation catalyst may further include a Group 6 metal (such as chromium or molybdenum) as a promoter.

Likewise, the transfer-hydrogenation conditions employed in the second reaction zone can be the same or similar to the conditions in the first reaction zone.

When using a reactive distillation, the first and second transfer-hydrogenation reaction zones may be located in the same column or in separate columns.

Similar to step (c) above, during the condensing step (g), water can be removed from the reaction mixture. Additionally, or alternatively, water can be separated from the third carbonyl compound before the third carbonyl compound is recycled to step (e).

The second aldol reaction (step (g)) can be carried out in presence of a catalyst at a temperature ranging from room temperature to 200° C. and a pressure ranging from atmospheric pressure to 1000 psig (6.9 MPa). Any catalyst known in the art to catalyze the aldol reaction can be utilized to catalyze the reaction.

In addition to water removal, the second crude aldol product can be further purified by distillation, extraction, decantation, or any other purification techniques known in the art before recycling to step (e).

A hydrogen donor of specific interest is iso-butanol (i-BuOH, see Eq. 3 below).

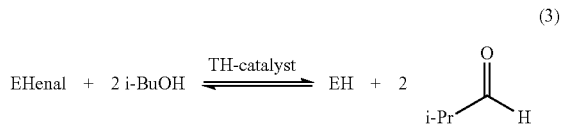

(3)

Equation 3 is similar to Equation 2, except that iso-butanol is substituted for n-butanol in the transfer-hydrogenation of 2EHenal. This reaction is of interest because of the pending commercial availability of iso-butanol as "biobutanol" and because of the significance of iso-butyraldehyde. Typically, iso-butyraldehyde is produced by hydroformylating propylene in an oxo reaction, which yields a mixture of n- and i-butyraldehyde. Controlling the n/i ratio in the oxo reaction is a significant technical challenge. The reaction in Equation 3, however, provides an independent method for producing only iso-butyraldehyde. Thus, it can be used to meet the growing demand for this valuable intermediate without co-producing the n-isomer.

Thus, in one embodiment of the process according to the invention, the first carbonyl compound is 2-ethylhexenal, the first alcohol compound is iso-butanol, the second carbonyl compound is iso-butyraldehyde, and the second alcohol compound is 2-ethylhexanol.

To engage the full advantages of reactive distillation, a boiling point criterion should be satisfied. That is, the products of a reaction should provide the most volatile and the least volatile components of a process mixture, which includes all of the reactants, intermediates, by-products, and products. If this criterion is met, then even reactions with unfavorable equilibrium constants can be driven to high conversion by selectively removing of the products through distillation. As shown in Table 1, it is common for aldehydes/ketones to have lower boiling points than their corresponding alcohols.

TABLE 1

Boiling Points of Some Alcohol/Carbonyl Pairs

| Alcohol | Boiling Point (° C.) | Aldehyde or Ketone | Boiling Point (° C.) | Diff. in Boiling Point (° C.) |
|---|---|---|---|---|
| Ethanol | 78 | Acetaldehyde | 21 | 57 |
| Isopropanol | 82 | Acetone | 56 | 26 |
| n-Butanol | 118 | n-Butyraldehyde | 75 | 43 |
| Crotyl Alcohol | 121 | Crotonaldehyde | 104 | 17 |
| i-Butanol | 108 | i-Butyraldehyde | 63 | 45 |
| 2EH | 184 | 2EHal | 163 | 21 |
| 2EHenol | 186 | 2EHenal | 175 | 11 |

Thus, a transfer-hydrogenation between a hydrogen donor alcohol that is of comparable boiling point to a recipient aldehyde (or ketone) can generate a much lower boiling aldehyde product and a much higher boiling alcohol product so that each of these may be removed from the top and bottom, respectively, of a transfer-hydrogenation reactive distillation column.

As noted above, instead of a reactive distillation column, it is possible to use a reaction pot to establish the transfer-hydrogenation equilibrium and a distillation head/fractionation column over the reaction pot to selectively remove the most volatile component. An advantage of this design is the opportunity to employ a homogeneous transfer-hydrogenation catalyst. Such catalysts often have higher activity for transfer-hydrogenation. There also can be advantages in the methods used for catalyst recovery and recycle.

The present invention includes and expressly contemplates any and all combinations of embodiments, features, characteristics, parameters, and/or ranges disclosed herein. That is, the invention may be defined by any combination of embodiments, features, characteristics, parameters, and/or ranges mentioned herein.

It is contemplated that any ingredient, component, or step that is not specifically named or identified as part of the invention may be explicitly excluded by at least some embodiments of the invention.

Any process, apparatus, compound, composition, embodiment, or component of the invention may be modified by the transitional terms "comprising," "consisting essentially of," or "consisting of," or variations of those terms.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

Any two numbers of the same property or parameter reported in the working examples may define a range. Those numbers may be rounded off to the nearest thousandth, hundredth, tenth, whole number, ten, hundred, or thousand to define the range.

The content of all documents cited herein, including patents as well as non-patent literature, is hereby incorporated by reference in their entirety. To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Abbreviations

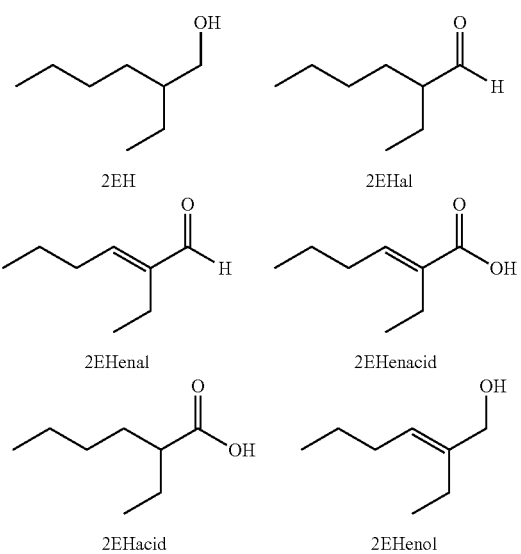

BTA represents butyraldehyde. NBNB represents n-butyl butyrate. IBIB represents isobutyl isobutyrate.

Materials n-Butanol, isopropanol, and Cu(NO$_3$)$_2$.2H$_2$O were purchased from Aldrich. 2-Ethyl-2-hexenal was purchased from TCI. γ-Al$_2$O$_3$ (⅛" pellets, pore volume 1.18 g H$_2$O/g support) was obtained from Alfa Aesar. La$_2$O$_3$ was obtained from NanoStructured & Amorphous Materials Inc. [Cu(CH$_3$COO)$_2$].H$_2$O was obtained from Mallinckrodt. K$_2$CO$_3$ was obtained from JT Baker.

Catalysts

The following Sponge Nickel™ and Sponge Cobalt™ catalysts, obtained from Johnson-Matthey, have the following compositions:

A=JM A-5000: 93.8% Ni/5.61% Al/0.1% Fe
B=JM A-7063: 92.8% Ni/5.45% Al/1.10% Mo
C=JM A-7604: 92.4% Ni/5.53% Al/0.12% Fe/1.57% Mo
D=JM A-5609: 94.8% Ni/4.51% Al/0.11% Fe/0.04% Mo
E=JM A-8646M: 3.67% Ni/2.52% Al/0.21% Fe/0.02% Mo/2.33% Cr/91.1% Co (sponge-cobalt)
F=HTC Ni 500 RP: Ni/Al The following Ni catalysts, obtained from BASF, have the following compositions:

G=Ni 3371: 50-70% Ni/0-2% Mo
H=Ni 3314: 50-70% Ni/0-2% Mo
I=Ni 3380: 50-70% Ni/0-2% Mo
J=Ni 3354: 50-70% Ni/0-2% Mo
K=Ni 3288: 50-70% Ni/0-2% Mo

The following Raney Nickel™ catalyst, obtained from Grace, has the following composition:

L=Ni 3288: 50-70% Ni/0-2% Mo

Synthesis of 10% Cu/γ-La$_2$O$_3$ catalyst (*Green Chemistry*, 12, 108-113 (2010)) (Catalyst M). An aqueous solution of cuprous acetate (4.94 g dissolved in 953 g of deionized water) was added to La$_2$O$_3$ (16.11 g) to form a slurry. An (aq) K$_2$CO$_3$ solution (5.79 g K$_2$CO$_3$ in 420 g deionized water) was added to the slurry until a pH of ~8 was obtained (405.9 g of the carbonate solution was added). The solution was stirred for 5 minutes and then stored overnight covered by aluminum foil. In the morning, the sample was decanted and the solid cake filtered and washed three times with 1 L of deionized water. The resulting solid was placed in a drying oven and the temperature ramped to 110° C. at 5° C./min, and held for 6 hr, then ramped to 450° C. at 5° C./min, and held for 4 hr, then cooled to room temperature.

Synthesis of 10% Cu/γ-Al$_2$O$_3$ catalyst (Catalyst N). An aqueous solution of CuNO$_3$(10.91 g dissolved in 24 g of deionized water) was added to γ-alumina (26.85 g) while mixing with a spatula. The resulting mixture was dried at 80° C. for 4 h, the temperature ramped to 120° C. at 5° C./min, and held for 2 hr, then to 400° C. at 5° C./min, and held for 2 hr, then cooled to room temperature.

All percentages above are in weight based on the total weight of the composition.

Analytical Methods
Gas Chromatographic Method

Process samples were analyzed by using an Agilent gas chromatograph Model 6890 equipped with a split/heated injector (250° C.) and a thermo couple detector (250° C.). A capillary column (30 meter×0.32 mm ID) coated with (50% methyl, 50% phenyl silicone) at 0.25 μm film thickness (such as DB-Wax or equivalent) was employed. Helium was used as the carrier gas with an initial column head pressure of 7.42 psi and an initial column flow of 1.56 mL/minute while the carrier gas linear velocity of 45 cm/second was maintained constant throughout the entire oven temperature program. The column temperature was programmed as follows: The initial oven temperature was set at 40° C. and was held for 3 minutes, the oven was ramped up to 200° C. at 8° C./minute and was held at 200° C. for 2 minutes (the total run time was 25 mins). The prepared sample solution (0.54) was injected with a split ratio of 75:1. EZ-Chrom Elite chromatography data system software was used for data acquisition and data processing. The sample preparation was done by weighing 0.1 g (accurate to 0.1 mg) of sample in a GC vial and adding 1.0 mL of ISTD solution (1% by volume of diethylene glycol dimethyl either in acetonitrile) to the GC vial.

Selectivity

Selectivities to C$_8$-species were calculated as the total moles of desired product formed from GC method divided by moles of 2-ethyl-2-hexenal reacted (moles of 2-ethyl-2-hexenal fed minus moles of 2-ethyl-2-hexenal left).

Similarly, selectivities to C$_4$ species were calculated as the total moles of desired product formed from GC method divided by moles of n-butanol reacted.

Conversion

Conversions were calculated relative to the moles of the α,β-unsaturated aldehyde, such as 2-ethyl-2-hexenal, submitted as reactant in a given transfer hydrogenation. The amount of reducing agent, H-donor, alcohol was varied with respect to the number of moles of α,β-unsaturated aldehyde.

Examples 1 and 2

A 100-mL titanium autoclave was charged with 24.5 g (407 mmol) of isopropanol, 10.2 g (81 mmol) of 2-ethyl-2-hexenal, and 2.7 g (40 mmol) of a washed Sponge Nickel™ catalyst identified in Table 2. The autoclave was pressurized with about 200 psig of nitrogen and then vented two times. It was then pressurized with 200 psig of nitrogen again and the closed autoclave was heated to the temperature reported in Table 2 and kept at reaction temperature for 4 h, cooled to room temperature, and depressurized. The liquid product was analyzed by gas chromatography. Conversion and selectivity data are given in Table 2.

Example 3

A 100-mL titanium autoclave was charged with 19.5 g (324 mmol) of isopropanol, 10.2 g (81 mmol) of 2-ethyl-2-hexenal, and 2.7 g (40 mmol) of a washed Sponge Nickel™ catalyst identified in Table 2. The autoclave was pressurized with about 200 psig of nitrogen and then vented two times. It was then pressurized with 200 psig of nitrogen again and the closed autoclave was heated to 180° C. and kept at reaction temperature for 4 h, cooled to room temperature, and depressurized. The liquid product was analyzed by gas chromatography. Conversion and selectivity data are given in Table 2.

Example 4

A 100-mL titanium autoclave was charged with 10.2 g (169 mmol) of isopropanol, 10.2 g (81 mmol) of 2-ethyl-2-hexenal, and 2.7 g (40 mmol) of a washed Sponge Nickel™ catalyst identified in Table 2. The autoclave was pressurized with about 200 psig of nitrogen and then vented two times. It was then pressurized with 200 psig of nitrogen again and the closed autoclave was heated to 180° C. and kept at reaction temperature for 4 h, cooled to room temperature, and depressurized. The liquid product was analyzed by gas chromatography. Conversion and selectivity data are given in Table 2.

TABLE 2

Transfer-Hydrogenation of 2EHenal with Isopropanol

| Ex. | Catalyst | Temp. (° C.) | Conv. of 2EHenal (%) | Selectivity (%) | | | | | |
|---|---|---|---|---|---|---|---|---|---|
| | | | | 2EHal | 2EHenol | 2EH | 2EH acids | Desired C8s | Acetone |
| 1 | A | 150 | 100 | 26.0 | 0.0 | 73.0 | 0.2 | 99.3 | >99.5 |
| 2 | A | 180 | 100 | 2.0 | 0.0 | 97.6 | 0.2 | 99.5 | >99.5 |
| 3 | A | 180 | 100 | 2.2 | 0.0 | 97.3 | 0.0 | 99.5 | >99.5 |
| 4 | A | 180 | 100 | 6.7 | 0.0 | 93.2 | 0.0 | 99.9 | >99.5 |

In Table 2, the amounts of 2EHacid and 2EHenacid were combined as 2EHacids.

The transfer-hydrogenation of 2EHenal with isopropanol catalyzed by a Sponge Nickel™ catalyst was examined in Examples 1-4. These examples show that the reaction proceeded cleanly to completion in less than four hours at 180°

C. Very little of the partially reduced products remained in the product solutions. The ratio of isopropanol:2EHenal was varied from 5:1 to 2:1 in Examples 2-4, and the relative yields of 2EH and 2-ethylhexanal (2EHal) directly reflected the influence of the relative excess $H_2$-donor. These examples revealed the excellent activity and selectivity of this catalyst for production of 2EH.

Examples 5-14

A 100-mL titanium autoclave was charged with 30.0 g (404 mmol) of n-butanol, 10.2 g (81 mmol) of 2-ethyl-2-hexenal, and 2.7 g (40 mmol) of a washed Sponge Nickel™ catalyst identified in Table 3. The autoclave was pressurized with about 200 psig of nitrogen and then vented two times. It was then pressurized with 200 psig of nitrogen again and the closed autoclave was heated to the temperature reported in Table 3 and kept at reaction temperature for 4 hours (Exs. 5-6 and 9-14) or 2 hours (Exs. 7 and 8), cooled to room temperature, and depressurized. The liquid product was analyzed by gas chromatography. Conversion and selectivity data are given in Table 3.

Example 15

A 100-mL titanium autoclave was charged with 45.0 g (606 mmol) of n-butanol, 15.3 g (121 mmol) of 2-ethyl-2-hexenal, 2.0 g (110 mmol; 3.3 wt %) of water, and 4.0 g (61 mol) of a washed Sponge Nickel™ catalyst identified in Table 3. The autoclave was pressurized with about 200 psig of nitrogen and then vented two times. It was then pressurized with 200 psig of nitrogen again and the closed autoclave was heated to 150° C. and kept at reaction temperature for 4 h, cooled to room temperature, and depressurized. The liquid product was analyzed by gas chromatography. Conversion and selectivity data are given in Table 3.

Example 16

A 100-mL titanium autoclave was charged with 45.0 g (606 mmol) of n-butanol, 15.3 g (121 mmol) of 2-ethyl-2-hexenal, 3.0 g (165 mmol; 5.0 wt %) of water, and 4.0 g (61 mol) of a washed Sponge Nickel™ catalyst identified in Table 3. The autoclave was pressurized with about 200 psig of nitrogen and then vented two times. Then it was pressurized with 200 psig of nitrogen again and the closed autoclave was heated to 150° C. and kept at reaction temperature for 4 h. It was then cooled to room temperature and depressurized. The liquid product was analyzed by gas chromatography. Conversion and selectivity data are given in Table 3.

Examples 17 and 18

A 100-mL titanium autoclave was charged with 30.0 g (404 mmol) of n-butanol, 10.2 g (81 mmol) of 2-ethyl-2-hexenal, and 2.7 g (40 mmol) of a washed Sponge Cobalt™ catalyst identified in Table 3. The autoclave was pressurized with about 200 psig of nitrogen and then vented two times. It was then pressurized with 200 psig of nitrogen again and the closed autoclave was heated to the temperature reported in Table 3 and kept at reaction temperature for 4 h, cooled to room temperature, and depressurized. The liquid product was analyzed by gas chromatography. Conversion and selectivity data are given in Table 3.

TABLE 3

Transfer-Hydrogenation of 2EHenal with n-Butanol

| Ex. | Catalyst | Temp. (° C.) | Conv. of 2EHenal (%) | 2EHal | 2EHenol | 2EH | 2EH acids | Desired C8s | BTA | NBNB | Butyric Acid |
|---|---|---|---|---|---|---|---|---|---|---|---|
| 5 | A | 150 | 78.5 | 77.3 | 2.4 | 7.7 | 11.4 | 87.3 | 87.5 | 0.0 | 12.5 |
| 6 | A | 180 | 95.0 | 72.7 | 0.7 | 14.3 | 11.2 | 87.7 | 95.9 | 0.0 | 14.1 |
| 7 | A | 150 | 60.3 | 78.5 | 4.2 | 7.0 | 9.8 | 89.7 | 97.7 | 0.0 | 12.3 |
| 8 | A | 180 | 89.5 | 82.8 | 1.5 | 9.8 | 5.0 | 94.2 | 90.3 | 0.0 | 9.7 |
| 9 | B | 150 | 70.4 | 81.2 | 3.1 | 0.0 | 14.4 | 84.3 | 100.0 | 0.0 | 0.0 |
| 10 | B | 180 | 96.4 | 79.2 | 0.0 | 14.3 | 5.2 | 93.5 | 88.6 | 4.4 | 11.4 |
| 11 | C | 150 | 79.3 | 82.9 | 3.2 | 5.5 | 8.0 | 91.7 | 87.9 | 0.3 | 11.8 |
| 12 | C | 180 | 98.9 | 93.0 | 0.5 | 18.0 | 6.1 | 101.4 | 98.5 | 1.0 | 0.5 |
| 13 | D | 150 | 57.2 | 89.2 | 0.8 | 0.3 | 8.4 | 90.2 | 98.7 | 0.5 | 0.9 |
| 14 | D | 180 | 79.6 | 84.2 | 0.8 | 7.5 | 5.7 | 92.6 | 92.0 | 0.4 | 7.6 |
| 15 | C | 150 | 736. | 88.9 | 3.3 | 4.6 | 2.0 | 96.8 | 88.7 | 0.7 | 10.6 |
| 16 | C | 150 | 78.4 | 85.7 | 2.5 | 4.6 | 5.4 | 92.9 | 80.2 | 0.8 | 19.0 |
| 17 | E | 150 | 25.0 | 83.5 | 10.7 | 1.9 | 3.2 | 96.1 | 78.9 | 10.6 | 10.5 |
| 18 | E | 180 | 73.1 | 81.0 | 7.6 | 5.6 | 4.9 | 94.2 | 22.9 | 34.7 | 42.5 |

In Table 3, the amounts of 2EHacid and 2EHenacid were combined as 2EHacids. Additionally, the amount of dibutyl acetal produced was included and combined with butyraldehyde (BTA).

The results from Examples 1-4 may be compared with those from Examples 5-6 in which n-butanol was replaced with isopropanol as the $H_2$-donor. As seen in Table 3, the conversion of 2EHenal was good, but inferior to the conversion in Examples 1-4. Moreover, the yield of 2EH was very low (7-14%). The reaction appeared to have been backed up at the saturated aldehyde stage, unable to convert to 2EH. That is, $K_4$ appeared to have been greater than $K_5$, as shown in Equations 4 and 5 below where $K_4$ is the equilibrium constant for reaction 4 and $K_5$ is the equilibrium constant for reaction 5.

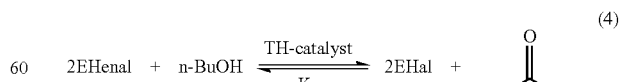

(4)

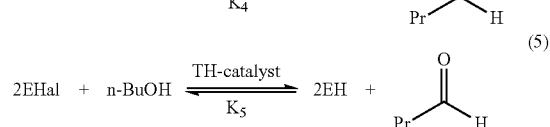

(5)

This invention provides a means for improving the conversion of 2EHenal to 2EH, as shown in Equations 4 and 5 above, by removing the product butyraldehyde from the top of the column based on its volatility (b.p.=75° C.) relative to the other components in the reaction zone (2EHenal b.p.=175° C.; n-butanol b.p.=118° C.; 2EHal b.p.=165° C.; and 2EH b.p.=184° C.). In addition, thermodynamic pressure to increase the conversion can be applied by feeding the reactants in the middle of a column packed with an appropriate catalyst, refluxing the intermediates in the column to allow for the separation of 2EHal (b.p.=163°) from 2EH (b.p.=184°), and selectively removing the product 2EH from the bottom of the column.

Example 19

A 100-mL titanium autoclave was charged with 45.0 g (606 mmol) of n-butanol, 15.3 g (121 mmol) of 2-ethyl-2-hexenal, and 4.0 g (61 mmol) of a washed Sponge Nickel™ catalyst (catalyst B). The autoclave was pressurized with about 200 psig of nitrogen and then vented two times. It was then pressurized with 200 psig of nitrogen again and the closed autoclave was heated to 150° C. and kept at reaction temperature for 6 h. Samples were removed from the autoclave at 60 min, 120 min, 180 min, 240 min, 300 min, and 360 min. The liquid samples were analyzed by gas chromatography. Conversion and selectivity data are given in Table 4.

TABLE 4

Transfer-Hydrogenation of 2EHenal with n-Butanol

| Time (min) | Conv. of 2EHenal (%) | Selectivity (%) | | | | | | | |
|---|---|---|---|---|---|---|---|---|---|
| | | 2EHal | 2EHenol | 2EH | 2EH acids | Desired C8s | BTA | NBNB | Butyric Acid |
| 60 | 23.6 | 65.4 | 16.7 | 3.5 | 9.2 | 85.6 | 89.4 | 1.1 | 9.5 |
| 120 | 45.4 | 81.5 | 6.7 | 3.2 | 5.9 | 91.4 | 92.0 | 1.2 | 6.8 |
| 180 | 58.9 | 78.5 | 5.1 | 4.0 | 4.1 | 87.6 | 93.7 | 0.7 | 5.6 |
| 240 | 66.3 | 85.5 | 4.3 | 4.5 | 3.9 | 94.3 | 93.0 | 0.6 | 6.5 |
| 300 | 73.2 | 82.5 | 6.9 | 5.3 | 3.5 | 94.7 | 91.2 | 0.8 | 8.0 |
| 360 | 80.0 | 81.5 | 7.0 | 6.2 | 3.8 | 94.6 | 89.9 | 0.4 | 9.6 |

In Table 4, the amounts of 2EHacid and 2EHenacid were combined as 2EHacids.

Example 20

A 100-mL titanium autoclave was charged with 45.0 g (606 mmol) of n-butanol, 15.3 g (121 mmol) of 2-ethyl-2-hexenal, and 4.0 g (61 mmol) of a washed Sponge Nickel™ catalyst (catalyst B). The autoclave was pressurized with about 200 psig of nitrogen and then vented two times. Then it was pressurized with 200 psig of nitrogen again and the closed autoclave was heated to 180° C. and kept at reaction temperature for 6 h. Samples were removed from the autoclave at 60 min, 120 min, 180 min, 240 min, 300 min and 360 min. The liquid samples were analyzed by gas chromatography. Conversion and selectivity data are given in Table 5.

TABLE 5

Transfer-Hydrogenation of 2EHenal with n-Butanol

| Time (min) | Conv. of 2EHenal (%) | Selectivity (%) | | | | | | | |
|---|---|---|---|---|---|---|---|---|---|
| | | 2EHal | 2EHenol | 2EH | 2EH acids | Desired C8s | BTA | NBNB | Butyric Acid |
| 60 | 40.2 | 5.3 | 4.8 | 10.3 | 6.5 | 90.3 | 89.0 | 2.1 | 8.9 |
| 120 | 74.5 | 83.8 | 3.3 | 8.0 | 2.9 | 95.1 | 92.9 | 0.3 | 6.8 |
| 180 | 87.9 | 83.9 | 2.1 | 9.5 | 2.7 | 95.5 | 91.9 | 0.6 | 7.5 |
| 240 | 95.7 | 82.3 | 1.3 | 12.7 | 1.8 | 96.4 | 89.5 | 1.3 | 9.2 |
| 300 | 97.6 | 80.3 | 1.1 | 15.6 | 1.6 | 96.9 | 88.2 | 2.0 | 9.8 |
| 360 | 99.0 | 77.7 | 0.4 | 18.3 | 1.3 | 96.4 | 87.4 | 2.2 | 10.4 |

In Table 5, the amounts of 2EHacid and 2EHenacid were combined as 2EHacids.

The data in Tables 4 and 5 show that the transfer-hydrogenation equilibria with Sponge Nickel™ catalysts were established over a 3 to 6-hour period at temperatures from 150 to 180° C.

Examples 21-25

A 300-mL Hastelloy C autoclave was charged with 90 g (1.21 mol) of n-butanol, 30 g (0.24 mol) of 2-ethyl-2-hexenal, and 20 mL of a BASF Ni catalyst (as specified in Table 6). The autoclave was pressurized with about 200 psig of nitrogen and vented two times, then pressurized with 200 psig of nitrogen again, and the closed autoclave was heated to 180° C. and kept at reaction temperature for 4 h. It was then cooled to room temperature and depressurized. The liquid product was analyzed by gas chromatography. Conversion and selectivity data are given in Table 6.

TABLE 6

Transfer-Hydrogenation of 2EHenal with n-Butanol and Ni Catalysts

| Ex. | Catalyst | Temp. (° C.) | Conv. of 2EHenal (%) | Selectivity (%) | | | | | | | |
|---|---|---|---|---|---|---|---|---|---|---|---|
| | | | | 2EHal | 2EHenol | 2EH | 2EH acids | Desired C8s | BTA | NBNB | Butyric Acid |
| 21 | G | 180 | 83.5 | 78.3 | 0.0 | 16.3 | 0.0 | 94.6 | 62.3 | 8.9 | 0.0 |
| 22 | H | 180 | 91.2 | 75.4 | 0.0 | 17.5 | 0.0 | 92.9 | 61.2 | 2.0 | 0.0 |
| 23 | I | 180 | 51.8 | 84.0 | 0.0 | 8.7 | 0.0 | 92.7 | 60.7 | 2.2 | 0.0 |
| 24 | J | 180 | 99.1 | 61.3 | 0.0 | 31.3 | 0.0 | 92.6 | 57.5 | 7.1 | 0.0 |
| 25 | K | 180 | 90.0 | 70.4 | 0.0 | 17.5 | 0.0 | 87.9 | 57.7 | 2.1 | 0.0 |

In Table 6, the amounts of 2EHacid and 2EHenacid were combined as 2EHacids. Additionally, the amount of dibutyl acetal produced was included and combined with butyraldehyde.

Examples 26-27

A 100-mL titanium autoclave was charged with 30.0 g (404 mmol) of n-butanol, 10.2 g (81 mmol) of 2-ethyl-2-hexenal, and 2.7 g (4.25 mmol) of 10 wt % $Cu/La_2O_3$. The autoclave was pressurized with about 200 psig of nitrogen and then vented two times. It was then pressurized with 200 psig of nitrogen again, and the closed autoclave was heated to the temperature reported in Table 7 and kept at reaction temperature for 4 h, cooled to room temperature, and depressurized. The liquid product was analyzed by GC. Conversion and selectivity data are given in Table 7.

Examples 28-29

A 100-mL titanium autoclave was charged with 30.0 g (404 mmol) of n-butanol, 10.2 g (81 mmol) of 2-ethyl-2-hexenal, and 2.7 g (4.25 mmol) of 10 wt % $Cu/Al_2O_3$. The autoclave was pressurized with about 200 psig of nitrogen and then vented two times. It was then pressurized with 200 psig of nitrogen again, and the closed autoclave was heated to the temperature reported in Table 7 and kept at reaction temperature for 4 h, cooled to room temperature, and depressurized. The liquid product was analyzed by GC. Conversions and selectivities are given in Table 7.

TABLE 7

Transfer-Hydrogenation of 2EHenal with n-Butanol and Cu Catalysts

| Ex. | Catalyst | Temp. (° C.) | Conv. of 2EHenal (%) | Selectivity (%) | | | | | | | |
|---|---|---|---|---|---|---|---|---|---|---|---|
| | | | | 2EHal | 2EHenol | 2EH | 2EH acids | Desired C8s | BTA | NBNB | Butyric Acid |
| 26 | M | 180 | 18.3 | 53.5 | 33.7 | 4.4 | 5.7 | 91.7 | 93.5 | 5.3 | 1.2 |
| 27 | M | 200 | 43.6 | 60.8 | 20.3 | 16.7 | 1.4 | 97.8 | 85.7 | 11.6 | 2.7 |
| 28 | N | 180 | 39.7 | 55.1 | 32.4 | 10.5 | 1.7 | 97.9 | 85.0 | 11.3 | 3.7 |
| 29 | N | 200 | 60.1 | 54.0 | 15.3 | 29.0 | 0.0 | 98.3 | 73.5 | 22.4 | 4.1 |

In Table 7, the amounts of 2EHacid and 2EHenacid were combined as 2EHacids.

A range of nickel- and copper-based heterogeneous catalysts have been examined in a continuous stirred-tank reactor (CSTR) mode—demonstrating activity for transfer-hydrogenation with good selectivity to desired $C_8$ products and n-butyraldehyde (see Tables 3, 6, and 7). However, the production of acetal by-products and butyric or 2EH acid was sometimes a slight problem.

Example 30

A 300-mL Hastelloy C autoclave was charged with 90 g (1.50 mol) of isopropanol 30 g (0.24 mol) of 2-ethyl-2-hexenal, and 16.6 g of Ni 3354 catalyst. The autoclave was pressurized with about 200 psig of nitrogen and vented two times. It was then pressurized with 200 psig of nitrogen again, and the closed autoclave was heated to 180° C. and kept at reaction temperature for 4 h. It was then cooled to room temperature and depressurized. The liquid product was analyzed by gas chromatography. Conversion and selectivity data are given in Table 8.

Example 31

A 300-mL Hastelloy C autoclave was charged with 90 g (1.21 mmol) of isobutanol, 30 g (0.24 mmol) of 2-ethyl-2-hexenal, and 16.6 g of Ni 3354 catalyst. The autoclave was pressurized with about 200 psig of nitrogen and then vented two times. It was then pressurized with 200 psig of nitrogen again, and the closed autoclave was heated to 180° C. and kept at reaction temperature for 4 h, cooled to room temperature, and depressurized. The liquid product was analyzed by gas chromatography. Conversion and selectivity data are given in Table 8.

was collected from base pot (1) and condenser (9) in base product tank (13). Samples were taken at points (15), (16) and (17).

Examples 32-37

The distillation unit described above was charged with 141 g of molybdenum-promoted Sponge Nickel™ catalyst A-7063, 1,664 g of 1-butanol, and 560 g of 2-ethylhexenal. This initial charge of catalyst was left in the base for the duration of the examples.

After bolting the base pot in place, the unit was leak checked, then purged with nitrogen by pressurizing to 50 psig and venting. This was repeated twice, then the unit was repressurized to 20 psig. The base was heated with an electric band heater until reflux and distillate takeoffs were established. A feed mix containing 5 moles of 1-butanol to every 1 mole of 2EHenal was then fed continuously to the base pot at a selected rate. Distillate was pumped back to the top of the column, and the base heat was adjusted to achieve the average reflux ratio shown in Table 9. Base takeoff was pumped out of the base through a sip tube that extended down 2.6 inches from the top of the inside of the base pot. The average base takeoff rate is also shown in Table 9.

After run conditions were established, samples of distillate and base takeoff were taken. At the end of the run session, the heating elements were turned off, and the unit was allowed to cool overnight. Material was left in the base for the next run session. Typical run sessions were 8 to 11 hours long. At the end of a session, the distillate takeoff tank and the base takeoff tank were drained, weights were obtained, and samples of this combined distillate takeoff and base takeoff were taken. All samples were analyzed by GC.

TABLE 8

Transfer-Hydrogenation of 2EHenal with Isopropanol and Isobutanol

| Ex. | Catalyst | H-donor | Conv. of 2EHenal (%) | Selectivity (%) | | | | | | |
|---|---|---|---|---|---|---|---|---|---|---|
| | | | | 2EHal | 2EHenol | 2EH | 2EH acids | Desired C8s | Acetone | Isobutyr-aldehyde |
| 30 | F | i-C$_3$OH | 100.0 | 0.0 | 0.0 | 97.9 | 0.0 | 97.9 | >99.5 | 0.0 |
| 31 | F | i-C$_4$OH | 100.0 | 49.6 | 0.0 | 31.2 | 16.9 | 80.8 | 0.0 | >99.5 |

In Table 8, the amounts of 2EHacid and 2EHenacid were combined as 2EH acids.

Reactive Distillation

The continuous reactive distillation experiments below were carried out in the unit (10) shown in FIG. 1. The unit (10) was equipped with a 3.5-L stirred base pot (1), a 48-inch by 1-inch column (2) packed with ¼" PRO-PAK® metal packing (available from Cannon Instrument Company), a feed pump (3), a reflux return pump (4), a base takeoff pump (5), column and line heaters (not shown), and a base heater (not shown). Reactions were performed under nitrogen pressure using a back-pressure regulator (6) and a cold trap (14) to control system pressure. The column condenser (7) and the two takeoff tank condensers (8, 9) were water cooled. Reactants were fed to base pot (1) from feed tank (11) by feed pump (3). The low boiling point product was condensed in condensers (7) and (8) and was collected in distillate product tank (12). Higher boiling point product

TABLE 9

Reactive Distillation of n-Butanol and 2EHenal

| | Example | | | | | |
|---|---|---|---|---|---|---|
| | 32 | 33 | 34 | 35 | 36 | 37 |
| Residence Time (h) | 5.7 | 5.0 | 5.5 | 22.3 | 18.0 | 18.0 |
| Reflux Ratio | 6.3 | 4.5 | 4.8 | 24.6 | 22.3 | 23.3 |
| Avg. Base Temp. (° C.) | 158 | 158 | 186 | 158 | 176 | 180 |
| Conv. of 2EHenal (%) | 94.8 | 94.5 | 98.5 | 97.1 | 99.4 | 99.7 |
| Selectivity (%) | | | | | | |
| 2EHal | 46.0 | 46.3 | 28.2 | 37.6 | 22.6 | 12.5 |
| 2EHenol | 1.1 | 1.5 | 0.1 | 0.3 | 0.4 | 0.8 |
| 2EH | 50.5 | 49.3 | 69.2 | 59.2 | 75.3 | 85.0 |
| 2EHacid | 1.5 | 1.6 | 0.4 | 0.5 | 0.2 | 0.1 |
| Desired C8s | 97.5 | 97.0 | 97.4 | 97.1 | 98.3 | 98.4 |
| BTA | 85.6 | 82.8 | 75.4 | 78.7 | 73.4 | 65.9 |

TABLE 9-continued

Reactive Distillation of n-Butanol and 2EHenal

| | Example | | | | | |
|---|---|---|---|---|---|---|
| | 32 | 33 | 34 | 35 | 36 | 37 |
| Dibutyl Acetal | 7.4 | 10.9 | 11.5 | 11.6 | 15.7 | 18.3 |
| NBNB | 2.1 | 1.8 | 3.3 | 2.2 | 2.8 | 4.4 |
| Butyric Acid | 1.5 | 1.0 | 1.5 | 1.6 | 1.6 | 1.1 |

Examples 9 and 10 show the limited conversion of 2EHenal to 2EH in an equilibrium reactor with no removal of low-boiling products. These examples may be compared with those carried out in the reactive distillation unit described above. The data in Table 9, in particular, show significantly increased yield of 2EH at temperatures from 158 to 186° C. The 2EH yields obtained in this continuous reactive distillation unit were 3 to 4 times greater than those obtained in the closed reactor without distillation.

Examples 38-41

The distillation unit described above was charged with 141 g of molybdenum-promoted Sponge Nickel™ catalyst A-7063, 1,664 g of i-butanol, and 560 g of 2-ethylhexenal. This initial charge of catalyst was left in the base for the duration of the examples.

After bolting the base pot in place, the unit was leak checked then purged with nitrogen by pressurizing to 50 psig and venting. This was repeated twice, and then the unit was repressurized to 20 psig. The base was heated with an electric band heater until reflux, and distillate takeoffs were established. A feed mix containing 5 moles of i-butanol to every 1 mole of 2EHenal was then fed continuously to the base pot at the desired rate. Distillate was pumped back to the top of the column, and the base heat was adjusted to achieve the average reflux ratio shown in Table 10. Base takeoff was pumped out of the base through a sip tube that extended down 2.6 inches from the top of the inside of the base pot. The average base takeoff rate is also shown in Table 10.

After run conditions were established, samples of distillate and base takeoff were taken. At the end of the run session, the heating elements were turned off, and the unit was allowed to cool overnight. Material was left in the base for the next run session. Typical run sessions were 8 to 11 hours long. At the end of a session, the distillate takeoff tank and the base takeoff tank were drained, weights were obtained, and samples of this combined distillate takeoff and base takeoff were taken. All samples were analyzed by GC.

TABLE 10

Reactive Distillation of i-Butanol and 2EHenal

| | Example | | | |
|---|---|---|---|---|
| | 38 | 39 | 40 | 41 |
| Residence Time (h) | 4.4 | 5.0 | 6.1 | 5.2 |
| Reflux Ratio | 4.5 | 5.0 | 7.6 | 5.4 |
| Avg. Base Temp. (° C.) | 177.0 | 179.0 | 190.0 | 191.0 |
| Conv. of 2EHenal (%) | 99.56 | 100.00 | 100.00 | 100.00 |
| Selectivity (%) | | | | |
| 2EHal | 24.5 | 24.8 | 25.2 | 24.7 |
| 2EHenol | 0.0 | 0.0 | 0.0 | 0.0 |

TABLE 10-continued

Reactive Distillation of i-Butanol and 2EHenal

| | Example | | | |
|---|---|---|---|---|
| | 38 | 39 | 40 | 41 |
| 2EH | 69.6 | 70.4 | 71.4 | 66.9 |
| 2EHacid | 0.0 | 0.0 | 0.0 | 0.4 |
| Desired C8s | 94.1 | 95.2 | 96.5 | 91.6 |
| i-BTA | 83.9 | 82.5 | 78.7 | 80.1 |
| Dibutyl Acetal | 11.3 | 12.9 | 16.4 | 9.8 |
| IBIB | 1.8 | 0.0 | 0.0 | 5.9 |
| i-Butyric Acid | 0.7 | 1.2 | 0.0 | 0.0 |

Examples 42-45

The distillation unit described above was charged with 100 g of Grace Nickel™ catalyst 3288, 1,664 g of i-butanol, and 560 g of 2-ethylhexenal. This initial charge of catalyst was left in the base for the duration of the examples.

After bolting the base pot in place, the unit was leak checked then purged with nitrogen by pressurizing to 50 psig and venting. This was repeated twice, and then the unit was repressurized to 20 psig. The base was heated with an electric band heater until reflux, and distillate takeoffs were established. A feed mix containing 5 moles of i-butanol to every 1 mole of 2EHenal was then fed continuously to the base pot at the desired rate. Distillate was pumped back to the top of the column and the base heat was adjusted to achieve the average reflux ratio shown in Table 11. Base takeoff was pumped out of the base through a sip tube that extended down 2.6 inches from the top of the inside of the base pot. The average base takeoff rate is also shown in Table 11.

After run conditions were established, samples of distillate and base takeoff were taken. At the end of the run session, the heating elements were turned off, and the unit was allowed to cool overnight. Material was left in the base for the next run session. Typical run sessions were 8 to 11 hours long. At the end of a session, the distillate takeoff tank and the base takeoff tank were drained, weights were obtained, and samples of this combined distillate takeoff and base takeoff were taken. All samples were analyzed by GC.

TABLE 11

Reactive Distillation of i-Butanol and 2EHenal

| | Example | | | |
|---|---|---|---|---|
| | 42 | 43 | 44 | 45 |
| Residence Time (h) | 4.6 | 4.0 | 3.6 | 3.9 |
| Reflux Ratio | 5.9 | 5.1 | 5.6 | 6.9 |
| Avg. Base Temp. (° C.) | 192.7 | 215.3 | 216.5 | 216.9 |
| Conv. of 2EHenal (%) | 99.57 | 99.50 | 98.81 | 98.82 |
| Selectivity (%) | | | | |
| 2EHal | 33.3 | 28.3 | 29.3 | 30.6 |
| 2EHenol | 0.0 | 0.0 | 0.0 | 0.0 |
| 2EH | 59.5 | 62.0 | 56.8 | 55.9 |
| 2EHacid | 0.0 | 0.0 | 0.0 | 0.0 |
| Desired C8s | 92.8 | 90.3 | 86.1 | 86.4 |
| i-BTA | 71.8 | 75.0 | 73.2 | 75.1 |
| Dibutyl Acetal | 20.5 | 18.9 | 21.0 | 20.6 |
| IBIB | 1.3 | 1.1 | 1.0 | 0.3 |
| i-Butyric Acid | 0.0 | 0.0 | 0.0 | 0.0 |

Examples 46-51

The distillation unit described above was used. A 170-mL catalyst basket was suspended in the base pot; extrudate nickel catalyst (Ni 3314) was charged to the basket. This initial charge of catalyst was left in the base for the duration of the examples.

After bolting the base pot in place, the unit was leak checked then purged with nitrogen by pressurizing to 50 psig then venting. This was repeated twice then the unit was repressurized to 70 psig. The base was heated with an electric band heater until reflux, and distillate takeoffs were established. A feed mix containing 5 moles of i-butanol to every 1 mole of 2EHenal was then fed continuously to the base pot at the desired rate. Some distillate was pumped back to the top of the column to achieve the average reflux ratio shown in Table 12. Base takeoff was pumped out of the base through a sip tube that extended down into the base pot liquid. The average base takeoff rate is shown in Table 12.

After run conditions were established, samples of distillate and base takeoff were taken. At the end of the run session, the heating elements were turned off, and the unit was allowed to cool overnight. Material was left in the base for the next run session. Reactions were done under nitrogen pressure using a back pressure regulator to control system pressure. The column condenser and the two tank condensers were water cooled. Typical run sessions were 8 to 11 hours long. At the end of a session, the distillate takeoff tank and the base takeoff tank were drained, weights were obtained, and samples taken of each. All samples were analyzed by GC.

TABLE 12

Reactive Distillation of i-Butanol and 2EHenal

| | Example | | | | | |
|---|---|---|---|---|---|---|
| | 46 | 47 | 48 | 49 | 50 | 51 |
| Residence Time (h) | 4.2 | 5.1 | 5.1 | 5.2 | 5.0 | 5.1 |
| Reflux Ratio | 8.0 | 7.2 | 8.8 | 6.9 | 7.1 | 6.7 |
| Avg. Base Temp. (° C.) | 178.8 | 190.2 | 190.3 | 201.1 | 198.3 | 199.0 |
| Conv. of 2EHenal (%) | 96.40 | 98.05 | 98.24 | 99.03 | 98.29 | 98.56 |
| Selectivity (%) | | | | | | |
| 2EHal | 42.8 | 26.6 | 25.9 | 20.5 | 22.3 | 21.2 |
| 2EHenol | 0.0 | 0.0 | 0.0 | 0.0 | 0.0 | 0.0 |
| 2EH | 42.5 | 60.4 | 62.6 | 65.4 | 64.5 | 65.7 |
| 2EHacid | 0.0 | 0.0 | 0.0 | 0.0 | 0.0 | 0.0 |
| Desired C8s | 85.3 | 87.1 | 88.5 | 86.0 | 86.7 | 86.9 |
| i-BTA | 59.9 | 61.9 | 61.3 | 66.7 | 62.2 | 61.7 |
| Dibutyl Acetal | 25.8 | 24.0 | 23.5 | 17.3 | 19.6 | 19.9 |
| IBIB | 1.0 | 1.5 | 2.2 | 3.9 | 5.0 | 4.7 |
| i-Butyric Acid | 0.0 | 0.0 | 0.0 | 0.0 | 0.0 | 0.0 |

Simulations

Aspen Plus V7.3 (Aspen Technology Inc.) was used for evaluating equilibrium conversions, investigating reactive distillation designs, and supporting experimental work. Components in the model include the primary reactions, plus components representing by-product reactions.

Table 13 shows the components and abbreviations used in the Aspen model. Two components were not present in Aspen's database and were entered based on their structures and all properties were estimated by Aspen using group contribution methods.

TABLE 13

Abbreviations for Simulation Results

| Component | Name | Formula | In Aspen Database |
|---|---|---|---|
| n-BuOH | n-butanol | $C_4H_{10}$ | yes |
| n-PrCHO | n-butyraldehyde | $C_4H_8O$ | yes |
| 2EHenal | 2-ethyl-2-hexenal | $C_8H_{14}O$ | yes |
| 2EH | 2-ethylhexanol | $C_8H_{18}O$ | yes |
| 2EHal | 2-ethylhexanal | $C_8H_{16}O$ | yes |
| $H_2O$ | Water | $H_2O$ | yes |
| NBNB | n-butyl butyrate | $C_8H_{16}O_2$ | yes |
| 2EHACET | 3-((1-butoxybutoxy)methyl)heptane | $C_{16}H_{34}O_2$ | no |
| ANALACET | 3-(dibutoxymethyl)heptane | $C_{16}H_{34}O_2$ | no |
| C7= | cis-2-heptene | $C_7H_{14}$ | yes |
| DNBAC | 1,1-dibutyoxybutane | $C_{12}H_{36}O_2$ | yes |

The vapor-liquid equilibrium (VLE) model used in the Aspen models was Uniquac, using Aspen database parameters when available, and estimating them based on UNIFAC when they were not available. No experimental work was performed to determine the unknown VLE parameters. This could have an effect on the reactive distillation estimates.

There are two primary reactions assumed to occur in all of the modeling results, and some results include four additional by-product reactions (Eqs. 8-11). All six reactions are shown in Table 14, with the equilibrium constant specifications. Aspen can either calculate the reaction equilibrium based on pure component Gibbs free energy, or the user can specify the equilibrium constant. Aspen's equilibrium constant predictions were not accurate for the by-product reactions and constant values were specified to approximate the amount of by-products found during experiments with base temperatures around 160° C. This is sufficient to simulate the qualitative presence of these by-products, but not the impact of column conditions on by-product formation.

TABLE 14

Reaction Stoichiometries and Equilibrium Constants for Examples 52-57

| Equation | Stoichiometry | Equilibrium Constant | In ($K_{eq}$) |
|---|---|---|---|
| 6 | n-BuOH + 2EHenal ↔ n-PrCHO + 2EHal | Aspen Calculated (temp. dependent) | |
| 7 | n-BuOH + 2EHal ↔ n-PrCHO + 2EH | Aspen Calculated (temp. dependent) | |
| 8 | 2EH + n-BuOH + n-PrCHO ↔ 2EHACET + $H_2O$ | 0.0067 | −5 |
| 9 | 2EHal + 2 n-BuOH ↔ ANALACT + $H_2O$ | 0.00034 | −8 |
| 10 | 2 n-PrCHO ↔ NBNB | 0.368 | −1 |
| 11 | 2 n-BuOH + n-PrCHO ↔ DNBAC + $H_2O$ | 0.0015 | −6.5 |

Examples 52-57

Table 15 contains Aspen simulations for comparison with Examples 32-37. The by-product reactions are present with fixed equilibrium constants, to simulate their presence and their destination in the distillation column, but the model cannot be used to predict the impact of operation conditions on the selectivity to by-products.

In these examples, heptene was fed into the model in a small amount to simulate the selectivity loss to this component, rather than modeling the reaction, which would involve adding $CO_2$ to the model. The column modeled for the results shown in Table 15 has 30 stages, which are significantly more than necessary for the separation, to simulate the experimental apparatus. Residence time is also not significant, since the model assumes reaction equilibrium occurs.

2EHenol, 2EHacid, and butyric acid were not in the model, but are included in the table for reference to Examples 32-37.

TABLE 15

Simulated Examples 52-57 for Comparison with Examples 32-37

| | Example | | | | | |
|---|---|---|---|---|---|---|
| | 52 | 53 | 54 | 55 | 56 | 57 |
| Residence Time (h) | 5.3 | 5.3 | 5.3 | 5.3 | 5.3 | 5.3 |
| Reflux Ratio | 6.3 | 4.5 | 4.8 | 24.6 | 22.3 | 23.3 |
| Avg. Base Temp. (° C.) | 158 | 158 | 186 | 158 | 176 | 180 |
| Conv. of 2EHenal (%) | 100 | 100 | 100 | 100 | 100 | 100 |
| Selectivity (%) | | | | | | |
| 2EHal | 40.1 | 41.4 | 39.9 | 21.9 | 24.0 | 24.6 |
| 2EHenol | 0.0 | 0.0 | 0.0 | 0.0 | 0.0 | 0.0 |
| 2EH | 58.7 | 57.4 | 58.9 | 76.9 | 74.8 | 74.2 |
| 2EHacid | 0.0 | 0.0 | 0.0 | 0.0 | 0.0 | 0.0 |
| Desired C8s | 98.8 | 98.8 | 98.8 | 98.8 | 98.8 | 98.8 |
| n-PrCHO | 87.7 | 88.7 | 89.3 | 87.5 | 87.7 | 80.1 |
| Dibutyl Acetal | 8.7 | 7.6 | 6.8 | 8.1 | 8.2 | 8.1 |
| NBNB | 0.10 | 0.10 | 0.10 | 0.01 | 0.03 | 0.03 |
| Butyric Acid | 0.0 | 0.0 | 0.0 | 0.0 | 0.0 | 0.0 |

Examples 58-68

These examples assume that only the first two reactions in Table 14 occur.

To demonstrate the concept of reactive distillation, simulations were performed over a variety of conditions with only the two main reactions. A brief description of the simulations is shown in Table 16. The simulation conditions and results are shown in Tables 17A and 17B.

TABLE 16

Simulation Description

| Ex. | Simulation | Description |
|---|---|---|
| 58 | equilibrium reactor at 180° C. | liquid-phase equilibrium reactor at 180° C. |
| 59 | equilibrium reactor at 150° C. | liquid-phase equilibrium reactor at 150° C. |
| 60 | 2-stage column | flashing reactor with condenser (2-stage column) |
| 61 | 2-stage column, high reflux | flashing reactor with condenser (2-stage column) |
| 62 | 15-stage column | 15-stage column with reaction in reboiler |
| 63 | 15-stage column, high reflux | 15-stage column with reaction in reboiler |
| 64 | 30-stage column, high reflux | 30-stage column with reaction in reboiler |
| 65 | 15-stage column, feed and reaction in middle of column | 15-stage column with reaction in middle (stages 7-12) |
| 66 | 15-stage column, feed and reaction in middle of column | 15-stage column with reaction in middle (stages 7-12) |
| 67 | 15-stage column, feed and reaction in middle of column, less excess butanol | 15-stage column with reaction in middle (stages 7-12), less excess butanol |
| 68 | 15-stage column, feed and reaction in middle of column, less excess butanol | 15-stage column with reaction in middle (stages 7-12), less excess butanol |

TABLE 17A

Simulation Conditions and Results

| | Example | | | | | |
|---|---|---|---|---|---|---|
| | 58 | 59 | 60 | 61 | 62 | 63 |
| Residence Time (h) | n/a | n/a | n/a | n/a | n/a | n/a |
| Reflux Ratio | n/a | n/a | 10.0 | 20.0 | 10.0 | 20.0 |
| Avg. Base Temp. (° C.) | 180 | 150 | 197.5 | 198.2 | 201.4 | 202.8 |
| Conv. of 2EHenal (%) | 100 | 100 | 100 | 100 | 100 | 100 |
| Selectivity (%) | | | | | | |
| 2EHal | 77.0 | 78.3 | 47.8 | 45.1 | 34.4 | 24.2 |
| 2EHenol | 0.0 | 0.0 | 0.0 | 0.0 | 0.0 | 0.0 |
| 2EH | 23.0 | 21.7 | 52.2 | 54.9 | 65.6 | 75.8 |
| 2EHacid | 0.0 | 0.0 | 0.0 | 0.0 | 0.0 | 0.0 |
| Desired C8s | 100 | 100 | 100 | 100 | 100 | 100 |
| n-PrCHO | 100 | 100 | 100 | 100 | 100 | 100 |
| Dibutyl Acetal | 0.0 | 0.0 | 0.0 | 0.0 | 0.0 | 0.0 |
| NBNB | 0.0 | 0.0 | 0.0 | 0.0 | 0.0 | 0.0 |
| Butyric Acid | 0.0 | 0.0 | 0.0 | 0.0 | 0.0 | 0.0 |

TABLE 17B

Simulation Condition and Results

| | Example | | | | |
|---|---|---|---|---|---|
| | 64 | 65 | 66 | 67 | 68 |
| Residence Time (h) | n/a | n/a | n/a | n/a | n/a |
| Reflux Ratio | 20.0 | 5.0 | 2.0 | 5.0 | 5.7 |
| Avg. Base Temp. (° C.) | 202.8 | 204.4 | 203.2 | 220.2 | 198.5 |
| Conv. of 2EHenal (%) | 100 | 100 | 100 | 100 | 100 |
| Selectivity (%) | | | | | |
| 2EHal | 24.2 | 13.8 | 29.1 | 32.9 | 5.7 |
| 2EHenol | 0.0 | 0.0 | 0.0 | 0.0 | 0.0 |
| 2EH | 75.8 | 86.2 | 70.9 | 67.1 | 94.3 |
| 2EHacid | 0.0 | 0.0 | 0.0 | 0.0 | 0.0 |
| Desired C8s | 100 | 100 | 100 | 100 | 100 |
| n-PrCHO | 100 | 100 | 100 | 100 | 100 |
| Dibutyl Acetal | 0.0 | 0.0 | 0.0 | 0.0 | 0.0 |
| NBNB | 0.0 | 0.0 | 0.0 | 0.0 | 0.0 |
| Butyric Acid | 0.0 | 0.0 | 0.0 | 0.0 | 0.0 |

As seen from Tables 16, 17A, and 17B, Examples 58 and 59 were for a CSTR assuming reaction equilibrium at 150 and 180° C., respectively. Examples 60 and 61 used just two stages on top of a boiling reactor to test the impact of having some vapor and reflux present. This modification increased the conversion to 2EH, but even very high reflux did not move the selectivity to 2EH much past 50%. Examples 62 and 63 used a 15-stage column, which pushed the selectivity up to 75% for a reflux ratio of 20. The results of Example 64 show that increasing the number of stages past 15 has no effect. Examples 65-68 were directed towards improving the reactive distillation design, with the reaction occurring in the middle of the column. Example 68 shows a design with a 94% selectivity to 2EH.

The data in Table 15 show excellent correspondence between the experimental results of continuous, reactive distillation and the results from an Aspen model of a continuous distillation unit. When combined with the data in Tables 17A and 17B, the results reveal a clear picture of (a) the influence of the reactive distillation effect on the conversion of 2EH to 2EHenal, (b) the value of the numbers of theoretical stages in the distillation column (more than 15 is not beneficial), and (c) the distinct improvement in 2EH production by operating the column in "feed-in-the-middle" mode. The simulation predicts that operating in this feed-in-the-middle mode can elevate the conversion to 2EH to 94%.

Examples 69-74

Aspen Plus simulations were performed for two other example chemistries, with similar theoretical results. These simulations only employed an equilibrium reaction model for the two primary reactions of hydrogen transfer, with no by-product reactions.

Examples 69-71 used isobutanol as the donor, and 2EHenal as the acceptor. Example 69 shows the predicted equilibrium result for a liquid-phase reactor at 180° C. Examples 70 and 71 show the improvement using reactive distillation, with reaction at the base and in the middle of the column, respectively.

Examples 72-74 used ethanol as the donor, and crotonaldehyde as the acceptor, with the fully hydrogenated product being n-butanol. Examples 72 and 73 show the predicted equilibrium result for a liquid reactor at 150 and 100° C., respectively. Example 74 shows the improvement for a reactive distillation, with the reaction at the base of the column.

A brief description of the simulations, conditions, and results are shown in Table 18.

TABLE 18

Description, Conditions, and Results of Simulation Examples

| Ex. | Donor/Acceptor | Configuration | Reflux Ratio | Base Reactor Temp. (° C.) | Conv. of Acceptor (%) | Conv. to 2EH or n-BuOH (%) |
|---|---|---|---|---|---|---|
| 69 | isobutanol/ 2EHenal | equilibrium reactor | n/a | 180.0 | 100 | 28.5 |
| 70 | isobutanol/ 2EHenal | reaction at column base | 5 | 161.5 | 100 | 73.3 |
| 71 | isobutanol/ 2EHenal | reaction in column middle | 5.8 | 199.5 | 100 | 96.9 |
| 72 | ethanol/ crotoaldehyde | equilibrium reactor | n/a | 150.0 | 100 | 66.6 |
| 73 | ethanol/ crotoaldehyde | equilibrium reactor | n/a | 100.0 | 100 | 66.1 |
| 74 | ethanol/ crotoaldehyde | reaction at column base | 5.0 | 124.0 | 100 | 95.1 |

Example 31, an experiment with iso-butanol as the hydrogen donor and no removal of low-boiling product, showed very similar characteristics to those with n-butanol, although Example 31 had somewhat greater conversion to 2EH at equilibrium (at 180° C., ~30%). This example may be compared with Examples 38-51, which were carried out in a reactive distillation unit. The latter examples showed significantly increased yield of 2EH at temperatures from 158 to 186° C. This trend correlates well with the Aspen simulation results. The simulations predict that the conversion to 2EH would increase from 29% in an equilibrium reactor (Example 69) to over 70% in a reactive distillation reactor (Example 70), and then to 97% with the reactive distillation reactor operating in feed-in-the-middle mode (Example 71).

It is interesting to note that transfer-hydrogenation with isopropanol achieved the same high-nineties level of conversion at equilibrium in a continuous flow stirred-tank reactor (CSTR) without reactive distillation enhancement (Example 30, 98% conversion to 2EH). Unfortunately, isopropanol is not available as a renewable resource and requires hydrogen for its production.

Examples 72-74 explored using ethanol as a transfer-hydrogenation hydrogen-donor in Aspen simulations for the conversion of crotonaldehyde to n-butanol. These calculations predict a significant advantage for operating this hydrogenation in reactive distillation mode. Equilibrium is driven to 95% completion by engaging reactive distillation in a CSTR (Example 74) and would, by analogy, be expected to be driven even closer to quantitative conversion by feed-in-the-middle mode.

Example 75

A 300-mL Hastelloy C autoclave was charged with 1.0 g of Ni-3314 extrudate in a catalyst basket. The autoclave was pressurized with about 200 psig of nitrogen and vented two times, and then it was pressurized with 50 psig of hydrogen. A flow of 0.53 SCFH hydrogen was started. Once the hydrogen flow was established, the autoclave was heated to 100° C. and kept at the same conditions (100° C. and 0.53 SCFH hydrogen flow rate) for 1 hour. In the meantime, a blowcase was charged with 54.0 g (896.7 mmol) of isopropanol and 83.0 g (828.7 mmol) of MIBK, and pressurized with 100 psig nitrogen. The content of the blowcase was heated to 180° C. The autoclave was then purged with 100 psig of nitrogen for 30 min. The material from the blowcase was blown to the autoclave using 500 psig of nitrogen. At t=0 min sample was taken once the reactor content equilibrated to 165° C. Samples were removed from the autoclave at 15 min, 30 min, 60 min, 90 min, 120 min, and 180 min. The liquid samples were analyzed by gas chromatography. Conversion and selectivity data are given in Table 19.

TABLE 19

Transfer-Hydrogenation of MIBK with iPrOH

| Time | Conversion (%) | | Selectivity (%) | |
|---|---|---|---|---|
| (min.) | MIBK | iPrOH | MIBC | Acetone |
| 15 | 13.4 | 13.6 | 93.3 | 98.3 |
| 30 | 20.7 | 20.3 | 95.6 | 98.5 |
| 60 | 30.5 | 29.4 | 97.7 | 96.5 |
| 90 | 35.5 | 34.2 | 98.2 | 94.9 |
| 120 | 38.5 | 36.8 | 98.3 | 94.9 |
| 180 | 40.7 | 39.6 | 98.5 | 93.7 |

Example 76

A 300-mL Hastelloy C autoclave was charged with 4.0 g of Ni-3314 extrudate in a catalyst basket. The autoclave was pressurized with about 200 psig of nitrogen and vented two times, and then it was pressurized with 50 psig of hydrogen. A flow of 0.53 SCFH hydrogen was started. Once the hydrogen flow was established, the autoclave was heated to 100° C. and kept at the same conditions (100° C. and 0.53 SCFH hydrogen flow rate) for 1 hour. In the meantime, a blowcase was charged with 51.4 g (855.5 mmol) of isopropanol, 85.4 g (853 mmol) of MIBK, and 14.9 of water (829.6 mmol), and pressurized with 100 psig nitrogen. The content of the blowcase was heated to 180° C. The autoclave was then purged with 100 psig of nitrogen for 30 min. The material from the blowcase was blown to the autoclave using 500 psig of nitrogen. A t=0 min sample was taken once the reactor content equilibrated to 165° C. Samples were removed from the autoclave at 15 min, 30 min, 60 min, 90 min, 120 min, and 180 min. The liquid samples were analyzed by gas chromatography. Conversion and selectivity data are given in Table 20.

TABLE 20

Transfer-Hydrogenation of MIBK with iPrOH in Presence of Water

| Time | Conversion (%) | | Selectivity (%) | |
|---|---|---|---|---|
| (min.) | MIBK | iPrOH | MIBC | Acetone |
| 15 | 18.7 | 17.2 | 92.9 | 89.1 |
| 30 | 24 | 22.2 | 94.9 | 90.1 |
| 60 | 32.1 | 30.6 | 96.3 | 90.2 |
| 90 | 36.1 | 34.8 | 96.7 | 88.8 |
| 120 | 38.5 | 37.3 | 96.5 | 90.6 |
| 180 | 40.3 | 39.7 | 98.6 | 89.2 |

Example 77

A 300-mL Hastelloy C autoclave was charged with 0.7 g of Ni-3314 extrudate in a catalyst basket. The autoclave was pressurized with about 200 psig of nitrogen and vented two times, and then it was pressurized with 50 psig of hydrogen. A flow of 0.53 SCFH hydrogen was started. Once the hydrogen flow was established, the autoclave was heated to 100° C. and kept at the same conditions (100° C. and 0.53 SCFH hydrogen flow rate) for 1 hour. In the meantime, a blowcase was charged with 40.6 g (674 mmol) of isopropanol and 77.0 g (673 mmol) of MAK, and pressurized with 100 psig nitrogen. The content of the blowcase was heated to 180° C. The autoclave was then purged with 100 psig of nitrogen for 30 min. The material from the blowcase was blown to the autoclave using 500 psig of nitrogen. A t=0 min sample was taken once the reactor content equilibrated to 165° C. Samples were removed from the autoclave at 15 min, 30 min, 60 min, 90 min, 120 min, and 180 min. The liquid samples were analyzed by gas chromatography. Conversion and selectivity data are given in Table 21.

TABLE 21

Transfer-Hydrogenation of MAK with iPrOH

| Time | Conversion (%) | | Selectivity (%) | |
|---|---|---|---|---|
| (min.) | MAK | iPrOH | MAC | Acetone |
| 15 | 8.5 | 12.3 | 93.3 | 72.3 |
| 30 | 15 | 19.1 | 94.6 | 70.5 |
| 60 | 20.5 | 25.2 | 95.8 | 74.4 |
| 90 | 26.7 | 32 | 96.1 | 77.1 |
| 120 | 31.3 | 36.9 | 96.7 | 76.2 |
| 180 | 38 | 42.3 | 95.2 | 82.3 |

The invention has been described in detail with particular reference to preferred embodiments thereof, but it will be understood that variations and modifications can be effected within the spirit and scope of the invention.

We claim:

1. A process for preparing a carbonyl compound and an alcohol compound, comprising:
    (a) contacting a first carbonyl compound with a first alcohol compound in the presence of a transfer-hydrogenation catalyst in a first reaction zone at conditions effective to form a second carbonyl compound from the first alcohol compound and a second alcohol compound from the first carbonyl compound;
    (b) removing the second carbonyl compound from the first reaction zone during step (a), and
    (c) condensing the second carbonyl compound in an aldol condensation reaction to produce the first carbonyl compound; and
    (d) passing the first carbonyl compound from the aldol condensation reaction to step (a);
    wherein the first carbonyl compound is a saturated aldehyde or ketone, or an α,β-unsaturated aldehyde or ketone,
    wherein the first alcohol compound is a primary or secondary alcohol, wherein the second alcohol compound is α,β-saturated,
    wherein the transfer-hydrogenation catalyst comprises a Group 8 to 11 metal; and wherein step (a) is carried out in a reactive distillation column.

2. The process according to claim 1, wherein the second carbonyl compound has the lowest boiling point and the second alcohol compound has the highest boiling point among all reactants, products, and by-products in the first reaction zone.

3. The process according to claim 1, wherein the first carbonyl compound comprises a saturated aldehyde or an α,β-unsaturated aldehyde.

4. The process according to claim 1, wherein the first carbonyl compound comprises a saturated ketone or an α,β-unsaturated ketone.

5. The process according to claim 1, wherein the first carbonyl compound has the formula (I), the first alcohol compound has the formula (II), the second alcohol compound has the formula (III), and the second carbonyl compound has the formula (IV):

(I)

(II)

(III)

(IV)

wherein
    $R^1$ is hydrogen, an alkyl group having 1-16 carbon atoms, or an aryl group having 6-20 carbon atoms;
    $R^2$ is an alkyl group having 1-16 carbon atoms, an aryl group having 6-20 carbon atoms, or an α,β-alkenyl group having 2-16 carbon atoms;
    $R^{2'}$ is an alkyl group having 1-16 carbon atoms or an aryl group having 6-20 carbon atoms;
    $R^3$ is hydrogen, an alkyl group having 1-16 carbon atoms, or an aryl group having 6-20 carbon atoms; and
    $R^4$ is an alkyl group having 1-16 carbon atoms or an aryl group having 6-20 carbon atoms.

6. The process according to claim 5, wherein the first alcohol compound is an iso-alcohol and the second carbonyl compound is an aldehyde or a ketone.

7. The process according to claim 5, wherein the first alcohol compound has 2 to 4 carbon atoms.

8. The process according to claim 5, wherein the first carbonyl compound is crotonaldehyde, mesityl oxide, butylidene acetone, isobutylidene acetone, 2,6-dimethylhepta-2,5-dien-4-one, 2-methyl-2-pentenal, 2-ethyl-2-hexenal, 2-propyl-2-heptenal, or 2,4-dimethyl-2-heptenal.

9. The process according to claim 5, wherein the first carbonyl compound is crotonaldehyde or 2-ethyl-2-hexenal, and wherein the first alcohol compound is ethanol, n-butanol, or iso-butanol.

10. The process according to claim 5, wherein the first carbonyl compound is 2-ethyl-2-hexenal, and wherein the first alcohol compound is iso-butanol.

11. The process according to claim 5, wherein the first carbonyl compound is methyl propyl ketone, methyl isopropyl ketone, methyl isobutyl ketone, methyl amyl ketone, diisobutyl ketone, diamyl ketone, diisoamyl ketone, 3-methylcyclohexanone, 3,5-dimethylcyclohexanone, 3-methyl-3-propylcyclohexanone, 3-methyl-3-isopropylcyclohexanone, 3,5,5-trimethylcyclohexanone, 4,6-dimethyl-2-heptanone, 4-methyl-2-nonanone, 2-methyl-4-nonanone, 4-heptanone, 4-methyl-2-heptanone, or 2-methyl-4-heptanone; and wherein the first alcohol compound is isopropanol.

12. The process according to claim 1, wherein the first carbonyl compound is crotonaldehyde, the first alcohol compound is ethanol, the second alcohol compound is n-butanol, and the second carbonyl compound is acetaldehyde.

13. The process according to claim 1, wherein the first carbonyl compound is 2-ethyl-2-hexenal, the first alcohol compound is n-butanol, the second alcohol compound is 2-ethylhexanol, and the second carbonyl compound is n-butyraldehyde.

14. The process according to claim 1, which further comprises:
(e) contacting a third carbonyl compound with the second alcohol compound in the presence of a second transfer-hydrogenation catalyst in a second reaction zone at conditions effective to form a fourth carbonyl compound from the second alcohol compound and a third alcohol compound from the third carbonyl compound;
(f) removing the fourth carbonyl compound from the second reaction zone during step (e),
(g) condensing the fourth carbonyl compound in an aldol condensation reaction to produce the third carbonyl compound; and
(h) passing the third carbonyl compound from the aldol condensation reaction to step (e).

15. The process according to claim 14, wherein the first carbonyl compound is crotonaldehyde, the first alcohol compound is ethanol, the second alcohol compound is n-butanol, the second carbonyl compound is acetaldehyde, the third carbonyl compound is 2-ethyl-2-hexenal, the third alcohol compound is 2-ethylhexanol, and the fourth carbonyl compound is n-butyraldehyde.

16. The process according to claim 1, wherein the second carbonyl compound is withdrawn from the column in an overhead stream and wherein the second alcohol compound is withdrawn from the column in a bottoms stream.

17. The process according to claim 1, wherein the reactive distillation column has 2 to 50 theoretical stages.

18. The process according to claim 17, wherein the reactive distillation column has 15 theoretical stages and wherein the first carbonyl compound and the first alcohol compound are introduced into the column at one or more theoretical stages 7 through 12, counting from top to bottom.

19. The process according to claim 1, wherein the transfer-hydrogenation catalyst comprises cobalt, nickel, copper, palladium, platinum, ruthenium, iridium, or combinations thereof.

20. The process according to claim 1, wherein the transfer-hydrogenation catalyst further comprises a Group 6 metal as a promoter.

21. The process according to claim 1, wherein the transfer-hydrogenation catalyst is a homogeneous catalyst.

22. The process according to claim 1, wherein the transfer-hydrogenation catalyst is a heterogeneous catalyst.

23. The process according to claim 1, wherein the molar selectivity to the second alcohol compound is at least 50%.

* * * * *